United States Patent
Tanabe et al.

(10) Patent No.: US 8,731,142 B2
(45) Date of Patent: May 20, 2014

(54) X-RAY COLLIMATOR

(71) Applicant: Accuthera Inc., Kawasaki (JP)

(72) Inventors: Eiji Tanabe, Kawasaki (JP); Masaaki Ito, Sagamihara (JP)

(73) Assignee: Accuthera Inc., Kawasaki (JP)

( * ) Notice: Subject to any disclaimer, the term of this patent is extended or adjusted under 35 U.S.C. 154(b) by 0 days.

(21) Appl. No.: 13/869,033

(22) Filed: Apr. 24, 2013

(65) Prior Publication Data

US 2013/0294583 A1 Nov. 7, 2013

(30) Foreign Application Priority Data

May 1, 2012 (JP) ................................ 2012-104302

(51) Int. Cl.
*G21K 1/04* (2006.01)
*A61N 5/10* (2006.01)

(52) U.S. Cl.
USPC ............. 378/150; 378/65; 378/147; 378/151; 250/505.1

(58) Field of Classification Search
USPC ................... 378/65, 147, 150, 151, 152, 153; 250/505.1
See application file for complete search history.

(56) References Cited

U.S. PATENT DOCUMENTS

| | | | | |
|---|---|---|---|---|
| 4,450,578 A | * | 5/1984 | Hill | ................................ 378/152 |
| 5,204,892 A | * | 4/1993 | Warden | ........................... 378/152 |
| 5,680,434 A | * | 10/1997 | Thelosen et al. | ............... 378/150 |
| 5,748,703 A | * | 5/1998 | Cosman | ........................ 378/152 |
| 7,106,831 B2 | * | 9/2006 | Li | ..................................... 378/152 |
| 7,109,506 B2 | * | 9/2006 | Papaioannou et al. | ..... 250/505.1 |
| 7,783,007 B2 | * | 8/2010 | Echner | .............................. 378/65 |
| 8,093,572 B2 | * | 1/2012 | Kuduvalli | .................. 250/505.1 |
| 2009/0074148 A1 | * | 3/2009 | Echner | ........................... 378/152 |
| 2013/0044860 A1 | * | 2/2013 | Nicholson et al. | .............. 378/62 |

FOREIGN PATENT DOCUMENTS

| | | |
|---|---|---|
| JP | H07-047142 A | 2/1995 |
| JP | 2008-536654 A | 1/2008 |
| JP | 2008-539833 A | 11/2008 |

* cited by examiner

*Primary Examiner* — Allen C. Ho
(74) *Attorney, Agent, or Firm* — Orion Consulting, Ltd.; Joseph P. Farrar, Esq.

(57) ABSTRACT

An X-ray collimator for controlling an X-ray radiation field, having a lower base member, a pair of regulating members, a pair of surrounding members having substantially U-shaped forms in planar view, N columnar members surrounded by the pair of surrounding members (where N is 4, 6, or 8), a guiding member, a pair of moving members moving parallel to the opposed surfaces of the regulating members, an upper base member, a first motor for horizontally moving the pair of moving members, and a second motor for moving the columnar members. The first motor is driven to horizontally move the pair of moving members over the same distance in opposite directions. The second motor is configured to move one of the columnar members along an internal surface of the surrounding member surrounding the columnar member, thereby moving the other N−1 columnar members sequentially.

8 Claims, 22 Drawing Sheets

(TOTALLY CLOSED STATE)

(TOTALLY CLOSED STATE)

(OCTAGONAL SHAPE)

(SQUARE SHAPE)

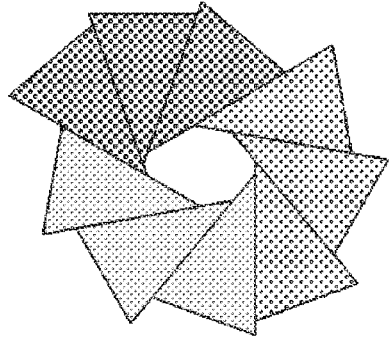
FIG. 24B
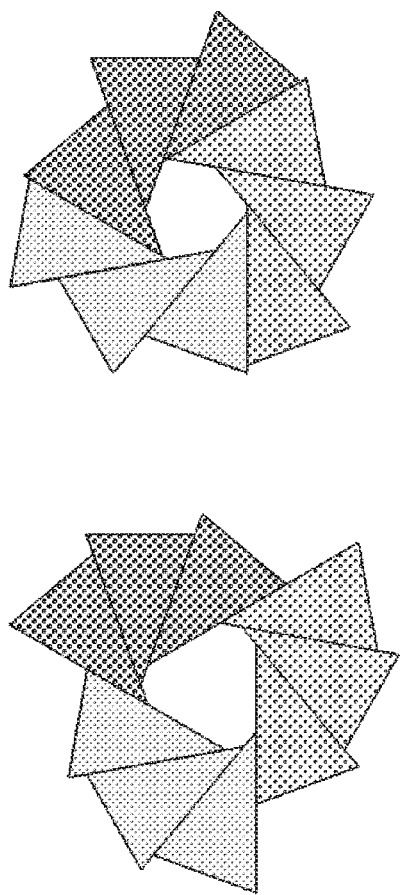
FIG. 24A
FIG. 24C
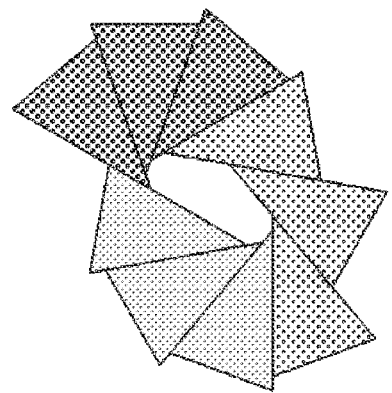
FIG. 24F
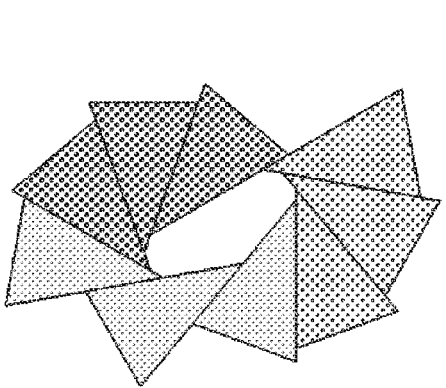
FIG. 24E
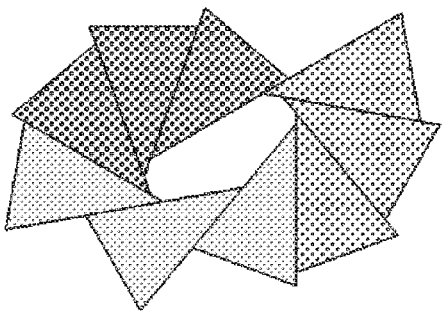
FIG. 24D

X-RAY COLLIMATOR

CROSS-REFERENCE TO RELATED APPLICATION

This application claims priority pursuant to 35 U.S.C. §119 to Japanese Patent Application No. 2012-104302, filed on May 1, 2012, the entire disclosure of which is incorporated by reference herein

BACKGROUND

1. Technical Field

Aspects of the example implementations relate to an improved X-ray collimator for controlling a radiation field shape when radiated X-rays are partially blocked to irradiate an affected area with therapeutic X-rays.

2. Related Art

In radiation (X-ray) therapy, a device such as a multileaf collimator is used for controlling a radiation field so as to make a radiated X-ray substantially coincide with the shape of an affected area. This multileaf collimator is composed of a combination of plate-like members, which are referred to as leaves, and rectangular in planar view with a heavy metal (tungsten, lead, etc.) as a material. The respective leaves constituting the multileaf collimator are intended to be independently subjected to movement control in the longitudinal directions of the leaves by an electrical driving source, so as to make the radiation field of therapeutic beams coincide with the shape of an affected area (for example, see Japanese Patent Application Laid-Open No. 2010-240085 (pp. 3-4, FIG. 2)). However, because the respective leaves constituting the multileaf collimator are rectangular in planar shape, the aperture shape of the leaves is a combination of linear shapes, and the shape of the radiation field is also defined by the linear shapes. Therefore, in order to apply radiation therapy to complex three-dimensional shapes such as tumors without causing damage to surrounding healthy tissues, there is room to improve the accuracy of forming the radiation field.

Accordingly, aperture diaphragms for collimating radiation have been proposed. For example, a mechanism for forming an iris aperture from six triangular leaves obtained by dividing a hexagon into six equal parts has been proposed, and this mechanism can change the minimum circular opening aperture from the minimum hexagonal opening to the maximum by use of the six triangular leaves (for example, see Japanese Patent Application Laid-Open No. 2008-536654). In addition, an apparatus has also been proposed which can change an aperture shape for transmitting X-rays between a circle with a first diameter and a circle with a second diameter by combining six blades for shielding X-rays and rotating rotation axes provided for each of the respective blades (for example, see Japanese Patent Application Laid-Open No. H09-512641). Furthermore, an apparatus has also been proposed which has a mechanism including four to six aperture blades and moving all of the aperture blades by the same adjustment stroke at the same time for forming an opening (aperture) using parts of the aperture blades (for example, see Japanese Patent Application Laid-Open No. 2008-539833).

However, the above-described collimators for adjusting the sizes of the apertures merely narrow the opening to circular or polygonal shapes to define the radiation fields for affected areas into circular shapes or polygonal shapes. Thus, since many affected areas are typically present in elongated shapes, there is a need for X-ray irradiation more than once in those cases. Therefore, there are problems such as the increased burden on patients, and radiation therapy has been desired which is completed with a minimum number of exposures.

SUMMARY

The present invention provides an X-ray collimator that can control an aperture to a slot shape, making it possible to make the X-ray radiation field elongated. Furthermore, the present invention also provides an X-ray collimator that can dynamically change the diameter or width of the X-ray radiation field from 1 mm or less to approximately 30 mm.

More specifically, the present invention provides an X-ray collimator for controlling an X-ray radiation field that includes a lower base member, a pair of regulating members, a pair of surrounding members having substantially U-shaped forms in planar view, N columnar members surrounded by the pair of surrounding members (where N is 4, 6, or 8), a guiding member, a pair of moving members configured to move parallel to the opposed surfaces of the regulating members, an upper base member, a first electrical driving source, and a second electrical driving source.

The lower base member serves as a base for the collimator. The pair of regulating members is provided vertically on the lower base member so as to have opposed surfaces parallel to each other. The pair of surrounding members has substantially U-shaped forms in planar view and a predetermined height, with the surrounding members sandwiched between the opposed surfaces of the regulating members in such a way that both U-shaped forms face each other. The N columnar members are surrounded by the pair of surrounding members, with each of the columnar members having a planar shape obtained by dividing a substantially regular polygon shape into N equal parts (where N is 4, 6, or 8). The guiding member has a rectangular shape in planar view, and is provided vertically on a protruding section extending from the lower base member so that the rectangular shape has a long side perpendicular to the opposed surfaces of the regulating members. The pair of moving members are moved parallel to the opposed surfaces of the regulating members in a manner that respectively follows both respective side surfaces of the guiding members, and are fixed on external surfaces of each of the pair of surrounding members adjacent to the guiding member. The upper base member is for fixing upper end surfaces of at least the regulating members. The first electrical driving source horizontally moves the pair of moving members and the second electrical driving source moves the columnar members.

The first electrical driving source is configured to horizontally move the pair of moving members over the same distance in opposite directions, thereby horizontally moving the pair of surrounding members over the same distance in opposite directions, the pair of surrounding members surrounding the columnar members. The second electrical driving source is configured to move one of the columnar members along an internal surface of the surrounding member surrounding the columnar member, thereby moving the other N−1 columnar members sequentially along internal surfaces of the surrounding members surrounding each of the other columnar members.

According to the aspects described above, the aperture can be controlled to a slot shape to form the X-ray radiation field into a slot shape, thereby achieving the advantageous effects of carrying out X-ray therapy for slot-shaped affected areas a reduced number of times and achieving an X-ray collimator capable of treating small tumors, which have not been able to be treated conventionally.

BRIEF DESCRIPTION OF THE DRAWINGS

A more complete appreciation of the invention and many of the attendant advantages thereof may be obtained as the same becomes better understood by reference to the following detailed description when considered in connection with the accompanying drawings, wherein:

FIGS. 19A through 25D are diagrams schematically illustrating other embodiments of the triangular prism members and their associated movements, illustrating changes in the size and shape of the aperture formed thereby.

DETAILED DESCRIPTION

An embodiment of the present invention will be described below with reference to the drawings. It is to be noted that although certain specific terminology is employed for the sake of clarity, the present disclosure is not limited to the specific terminology so selected and it is to be understood that each specific element includes all technical equivalents that have a similar function, operate in a similar manner, and achieve a similar result.

Further, an understanding of the present invention will be facilitated in the following description by describing component parts in order of assembly to complete the apparatus, X-ray collimator 100. It is to be noted that the order of the parts assembly does not always coincide with the order of assembling an actual apparatus. In addition, while the "the left-hand side in the figure" and "the right-hand side in the figure" are regarded respectively as "the front of the apparatus" and "the back of the apparatus" in the respective plan views and the respective perspective views for ease of explanation, which orientation is regarded as the front or back of the apparatus depends on the actual usage mode in the case of real apparatuses.

As will become apparent, the X-ray collimator 100 according to the embodiment described herein is an apparatus that allows a radiation field of X-rays radiated from above to be narrowed into a slot shape through an aperture. In addition, a metal block 60 composed of six triangular prism members 4a to 4f will be described as an example thereof in the following embodiment of the present invention. These six triangular prism members 4a to 4f each have a planar shape obtained by dividing a substantially regular hexagon into six equal parts. Thus, when the planar shapes of the six triangular prism members 4a to 4f are combined, a substantially regular hexagon is obtained.

(Apparatus Mechanism)

Figure 1A:
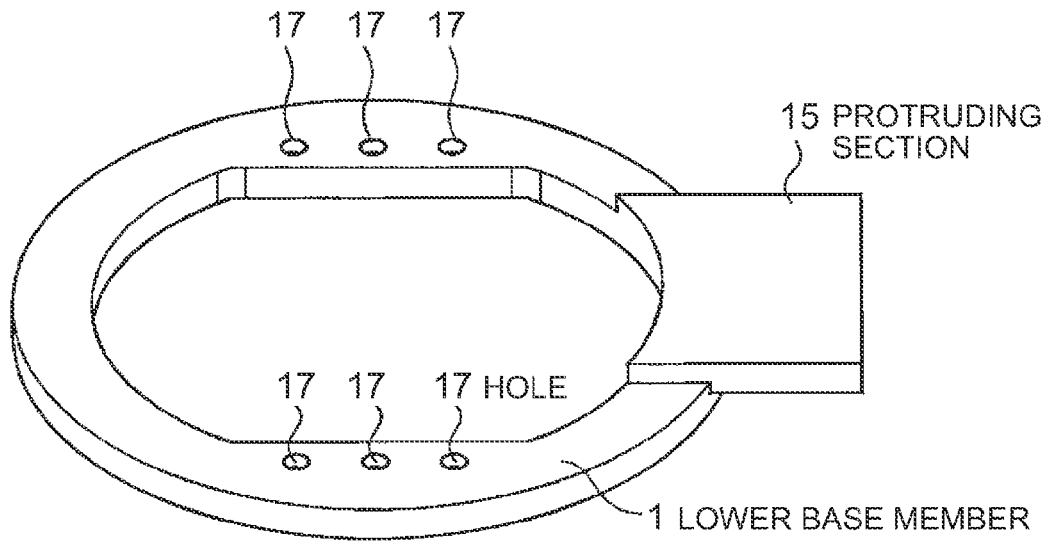
FIGS. 1A and 1B are respectively a perspective view and a plan view of a lower base member.
Figure 1B:
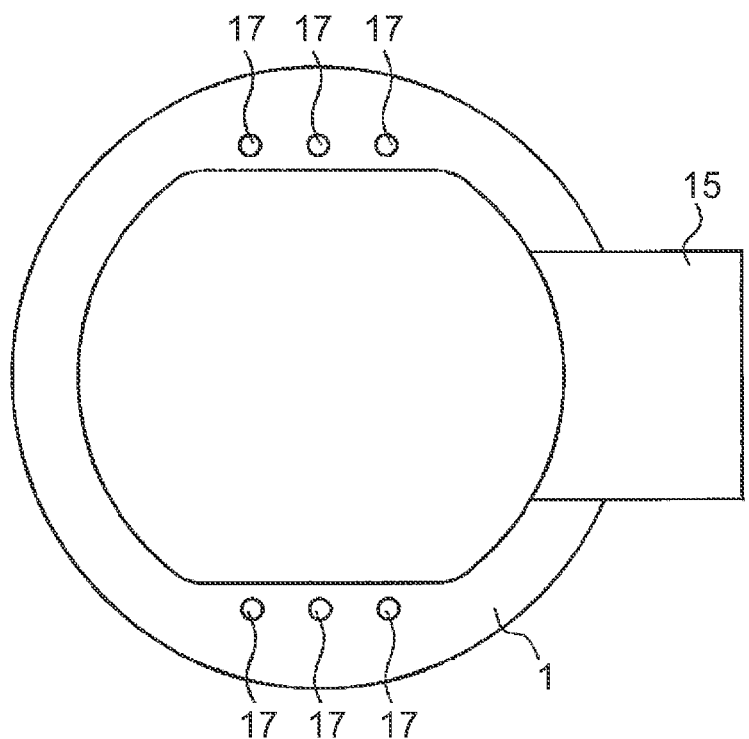
Figure 2A:
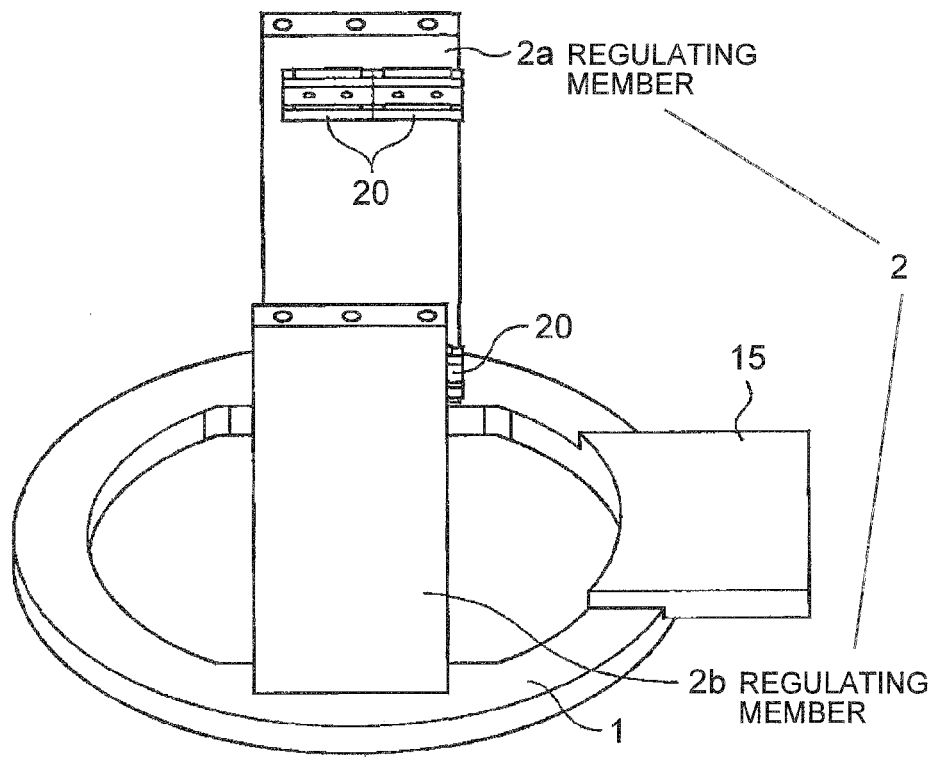
FIGS. 2A and 2B are respectively a perspective view and a plan view of regulating members and provided vertically thereon.
Figure 2B:
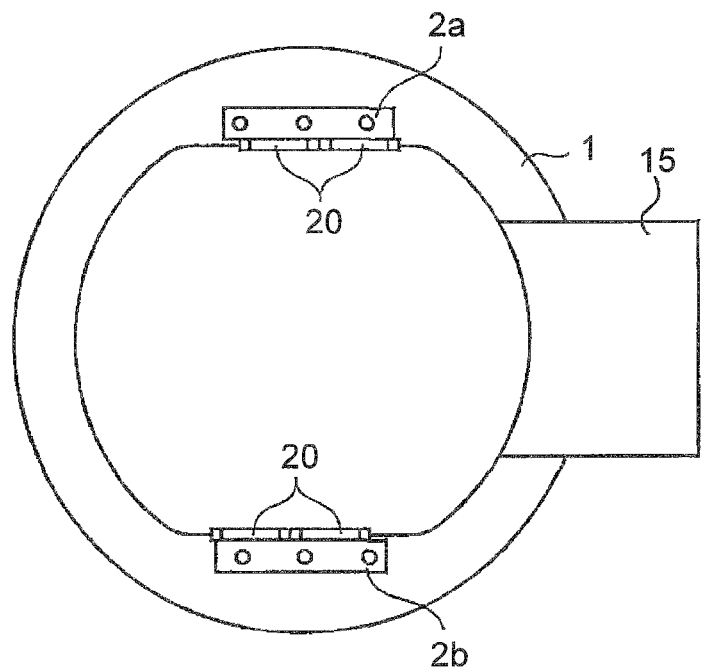

FIGS. 1A and 1B and FIGS. 2A and 2B are diagrams illustrating a structure which has a pair of regulating members 2 (2a and 2b) mounted on a lower base member 1. FIG. 1A is a perspective view of the lower base member 1, whereas FIG. 1B is a plan view thereof, and FIG. 2A is a perspective view of the structure in FIGS. 1A and 1B, mounting the pair of regulating members 2a and 2b, whereas FIG. 2B is a plan view of the structure. The lower base member 1 is a member which serves as a base for the apparatus. The lower base member 1 is a substantially annular member in planar view, and this annular shape has therein a hollow formed in a substantially elliptical planar shape. A protruding section 15 extending from a portion of the inner edge of the annular section of the lower base member 1 toward the back of the apparatus (the right-hand side in the figure), is configured integrally with the lower base member 1, and manufactured from aluminum. The protruding section 15 is thicker than the lower base member 1 and is rectangular in planar view. The protruding section 15 has an arc-like side in plan view on the front of the apparatus (the left-hand side in the figure), and this arc-like side constitutes a portion of the inner edge of the annular shape of the lower base member 1.

Further, the annular shape of the lower base member 1 has two rows of three horizontal holes 17 formed to be opposed to each other with the substantially elliptical hollow interposed therebetween in planar view, making six holes 17 in total. In addition, the regulating members 2a and 2b are provided vertically on the lower base member 1, so as to have their opposed surfaces parallel to each other. The pair of regulating members 2a and 2b are thick plate-like members which are generally elongate in appearance in transverse direction in the figure, and rectangular in planar shape. The pair of regulating members 2a and 2b is, at the bottoms thereof, fastened with screws through the holes 17 of the lower base member 1.

Figure 9A:
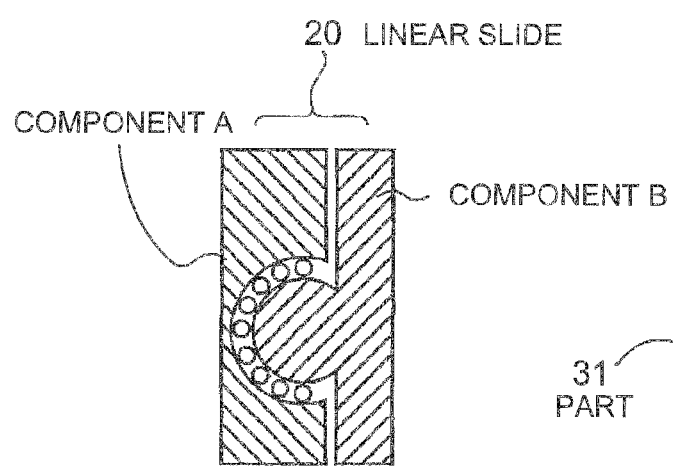
FIGS. 9A and 9B are respectively enlarged diagrams schematically illustrating vertical sections of a linear slide and a bearing.

In addition, each of the pair of regulating members 2a and 2b has, on opposed surfaces thereof, horizontally extending linear slides 20 provided near the upper end and lower end of the opposed surfaces. The many linear slides 20 used in the apparatus will be briefly described now with reference to the enlarged vertical section of FIG. 9A. The linear slide 20 is composed of a component B with an arc-like projection and a component A with a groove mating with the projection, and a number of small balls (bearings) are provided around the projection of the component B. Further, the component A is attached to one member, whereas the component B is attached to the other member, so that the members both can smoothly slide over each other in a vertical direction in the figure. It is to be noted that the shapes of the projections of the component B and the groove of the component A do not necessarily have to be those shown FIG. 9A, and may have any shape as long as the projection of the component B and the groove of the component A are configured slidably to mate with each other.

Figure 3A:
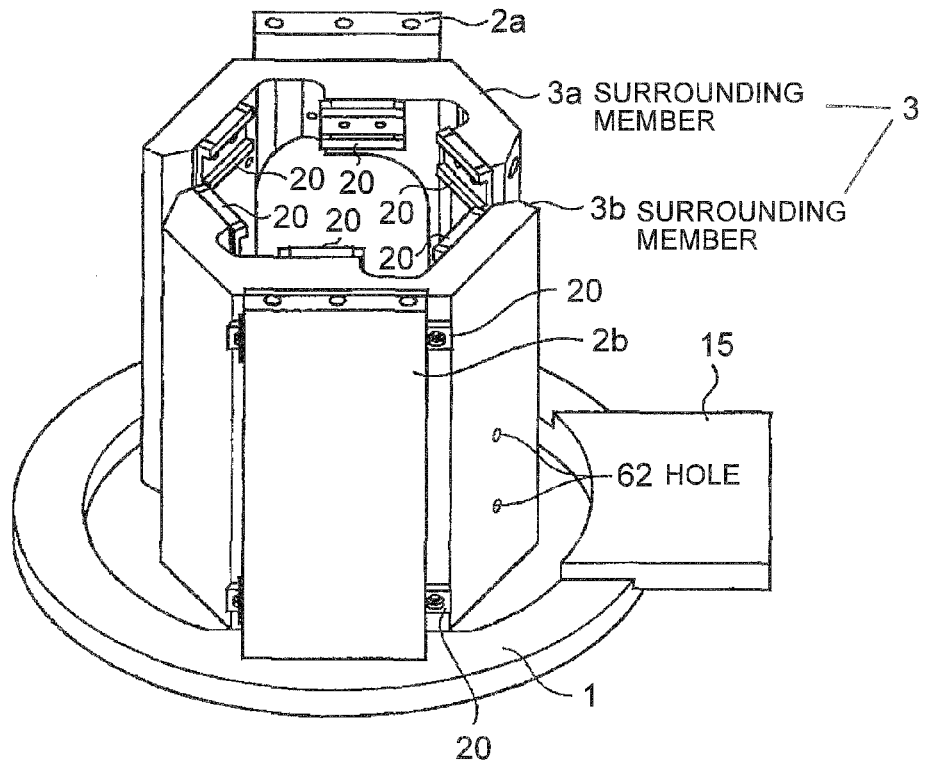
FIGS. 3A and 3B are respectively a perspective view and a plan view of a structure mounted with a pair of surrounding members.
Figure 3B:
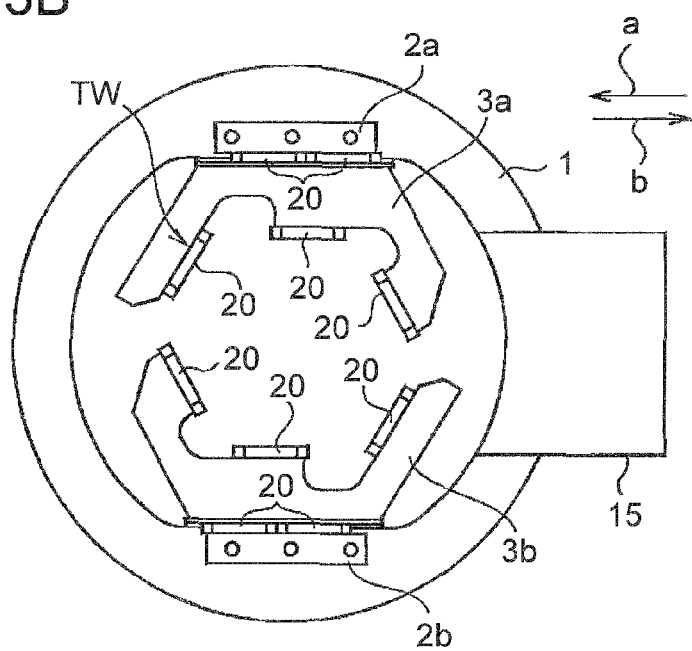

Next, the structure in FIGS. 2A and 2B, mounting a pair of surrounding members 3 (3a, 3b) will be described with reference to FIGS. 3A and 3B. FIG. 3A is a perspective view, whereas FIG. 3B is a plan view. The pair of surrounding members 3a and 3b are members which are substantially U-shaped in planar view, and lower in height than the regulating members 2a and 2b, and each have three continuous wall surfaces because of being the substantially U-shaped in planar view. These three wall surfaces are referred to as "internal surfaces (inside wall surfaces)" toward the center of apparatus, and as "external surfaces (outside wall surfaces)" toward the outside of the apparatus. Further, the pair of surrounding members 3a and 3b is arranged to be sandwiched between the opposed surfaces of the regulating members 2a and 2b, in such a way that the U-shaped forms of the surrounding members 3a and 3b face each other.

In addition, as described previously, the regulating member 2a is, near the upper end and lower end thereof, provided with the linear slides 20 extending horizontally and the surrounding member 3a are thus also provided with linear slides 20 in the corresponding positions of the external surface. Likewise, the surrounding member 3b are, on the external surface thereof, also provided with linear slides 20 to correspond to the linear slides 20 extending horizontally near the upper end and lower end of the regulating member 2b.

Thus, the surrounding member 3a is able to slide in the longitudinal direction of the rectangle in planar view with respect to the regulating member 2a provided vertically on the lower base member 1, whereas the surrounding member 3b is able to slide in the longitudinal direction of the rectangle in planar view with respect to the regulating member 2b provided vertically on the lower base member 1. More specifically, the surrounding members 3a and 3b are able to move horizontally in the front-back direction (in the right-left direction in FIG. 3B) of the apparatus (see the arrows of symbols a and b in FIG. 3B). In addition, the three wall surfaces of the surrounding member 3a are, near the upper ends and lower ends of the respective internal surfaces thereof, provided with linear slides 20 in the horizontal direction, whereas the three wall surfaces of the surrounding member 3b are, near the upper ends and lower ends of the respective internal surfaces thereof, also provided with linear slides 20 in the horizontal direction.

Furthermore, the outside wall surfaces of the surrounding members 3a and 3b on the back of the apparatus (the right-hand side of the figure) have, in positions lower than the intermediate positions in the vertical directions thereof, a pair of holes 62 formed in the vertical directions. The pair of holes 62 is intended to fix moving members 6a and 6b as will be described later. It is to be noted that the surrounding members 3a and 3b are not fixed to the lower base member 1, and the linear slides 20 near the lower ends of the internal surfaces of the surrounding members 3a and 3b, the holes of the surrounding member 3a for fixing the moving member, etc. are not shown in the figures.

Figure 4A:
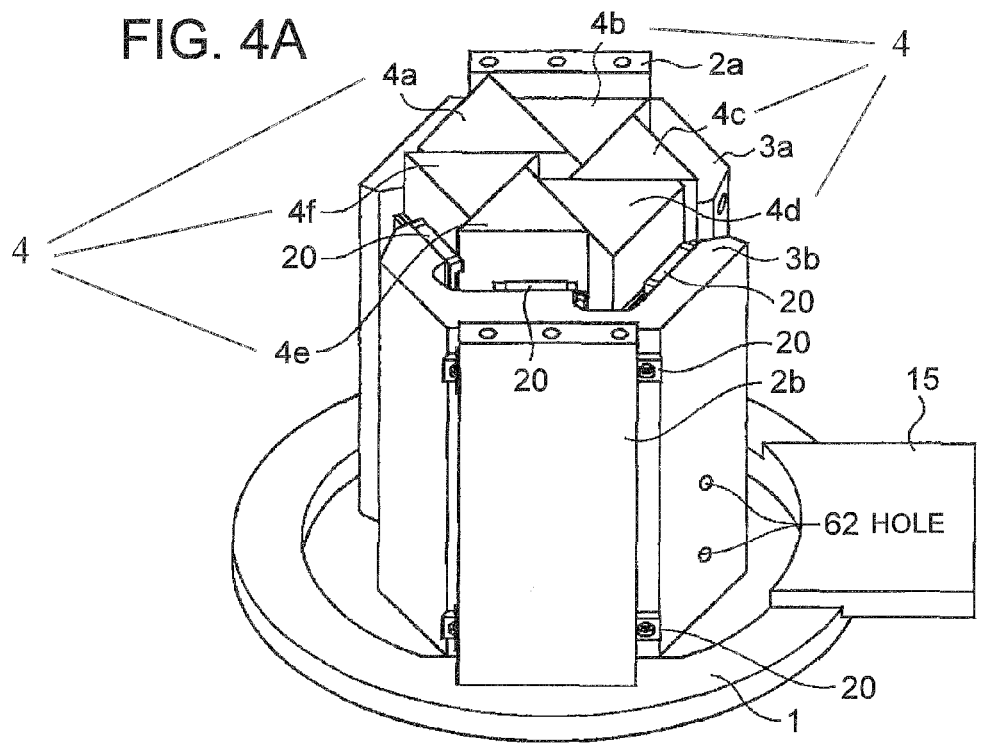
FIGS. 4A and 4B are respectively a perspective view and a plan view of the structure mounted with triangular prism members.
Figure 4B:
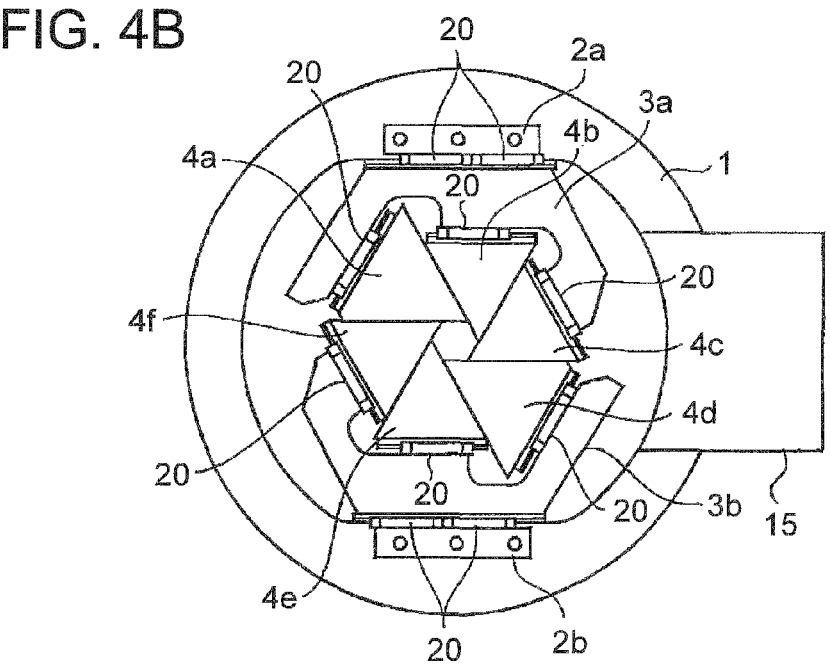

Next, the structure in FIGS. 3A and 3B mounting the six triangular prism members 4 (4a to 4f) will be described with reference to FIGS. 4A and 4B. FIG. 4A is a perspective view, whereas FIG. 4B is a plan view. It is to be noted that, for the sake of simplicity, the reference numeral 20 indicating the linear slides provided on the surrounding member 3b are omitted wherever possible in the following drawings.

First, the metal block 60 composed of the six triangular prism members 4a to 4f will be described with reference to FIG. 12. These six triangular prism members 4a to 4f are made of a heavy metal material that blocks X-rays, such as tungsten (W). The respective triangular prism members 4a to 4f are, on the outside vertically long rectangular surfaces thereof, provided with a pair of upper and lower linear guides 20 extending horizontally.

The linear slides 20 provided on each of the triangular prism members 4a, 4b, and 4c and the linear guides 20 provided on the surrounding member 3a mate with each other to make the surrounding member 3a and each of the triangular prism members 4a, 4b, and 4c able to smoothly slide over each other in a horizontal direction. Likewise, the linear slides 20 provided on each of the triangular prism members 4d, 4e, and 4f and the linear guides 20 provided on the surrounding member 3b mate with each other to make the surrounding member 3b and each of the triangular prism members 4d, 4e, and 4f able to smoothly slide over each other in a horizontal direction. The set of three triangular prism members 4a, 4b, and 4c are moved horizontally by the horizontal movement of the surrounding member 3a. Likewise, the set of three triangular prism members 4d, 4e, and 4f are moved horizontally by the horizontal movement of the surrounding member 3b.

Further, the six triangular prism members 4a to 4f constituting the metal block 60 are assembled together to provide a substantially regular hexagon in planar shape. In other words, the triangle shape in planar view for each of the triangular prism members 4a to 4f is obtained by evenly dividing the substantially regular hexagon into six parts. The term substantially regular hexagon is used herein because the length of one side of the triangle shape in planar view for the triangular prism members 4a and 4d is slightly longer than the length of one side of the triangle shape in planar view for the triangular prism members 4b, 4c, 4e and 4f. Additionally, these six triangular prism members 4a to 4f (metal block 60) are surrounded by the pair of surrounding member 3a and 3b. In addition, among the six triangular prism members 4a to 4f, a bearing (shown in FIG. 9B) is interposed between the upper ends of mutually facing vertically long rectangular side surfaces of triangular prism members (4a and 4b, 4b and 4c, 4c and 4d, 4d and 4e, 4e and 4f, 4f and 4a) which are adjacent to each other.

Figure 9B:
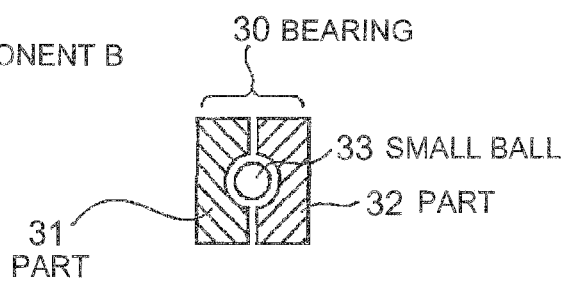

FIG. 9B shows an enlarged vertical section of the bearing. The bearing 30 is configured to have a number of small ball bearings 33 rollingably sandwiched in a groove (extending in a direction perpendicular to the plane of paper) between a part 31 and a part 32. The part 31 of the bearing 30 is provided on a side of the triangle shape in planar view for one of the triangular prism members 4 (for example, 4a), whereas the part 32 thereof is provided on a side of the triangle shape in planar view for the triangular prism member 4 (for example, 4b) adjacent to the previous triangular prism member 4 (4a), with the side facing the side with the part 31 provided thereon. In brief, the bearing 30 is provided on all points where sides of triangle shapes in cross section face each other, at the upper ends of the triangular prism members 4 (4a to 4f), so that the adjacent triangular prism members thus move smoothly with respect to each other. Therefore, when the triangular prism member 4a is moved, this movement sequentially moves the other triangular prism members 4b, 4c, 4d, 4e, and 4f.

Figure 10:
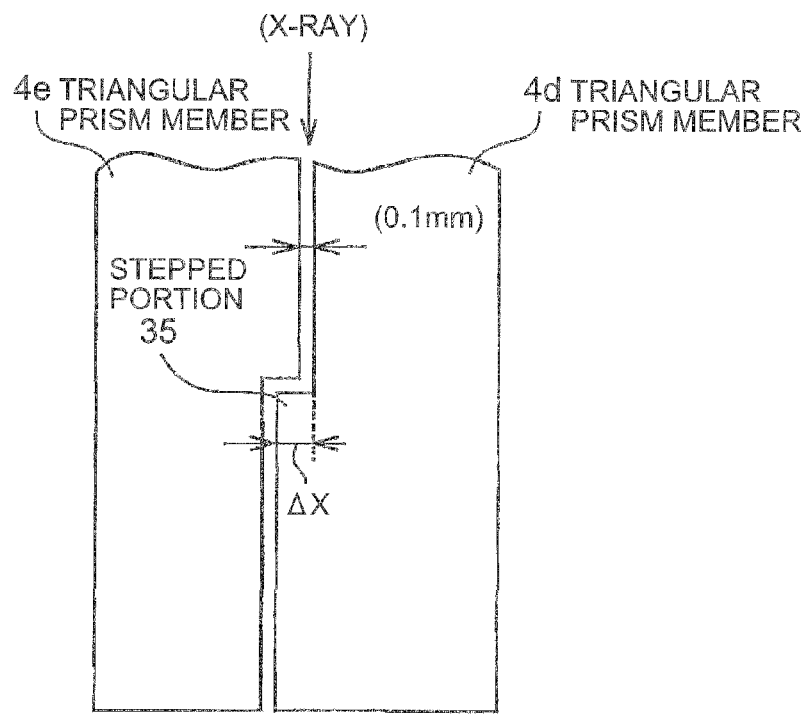
FIG. 10 is a diagram schematically illustrating a stepped portion provided for the triangular prism member 4.
Figure 12:
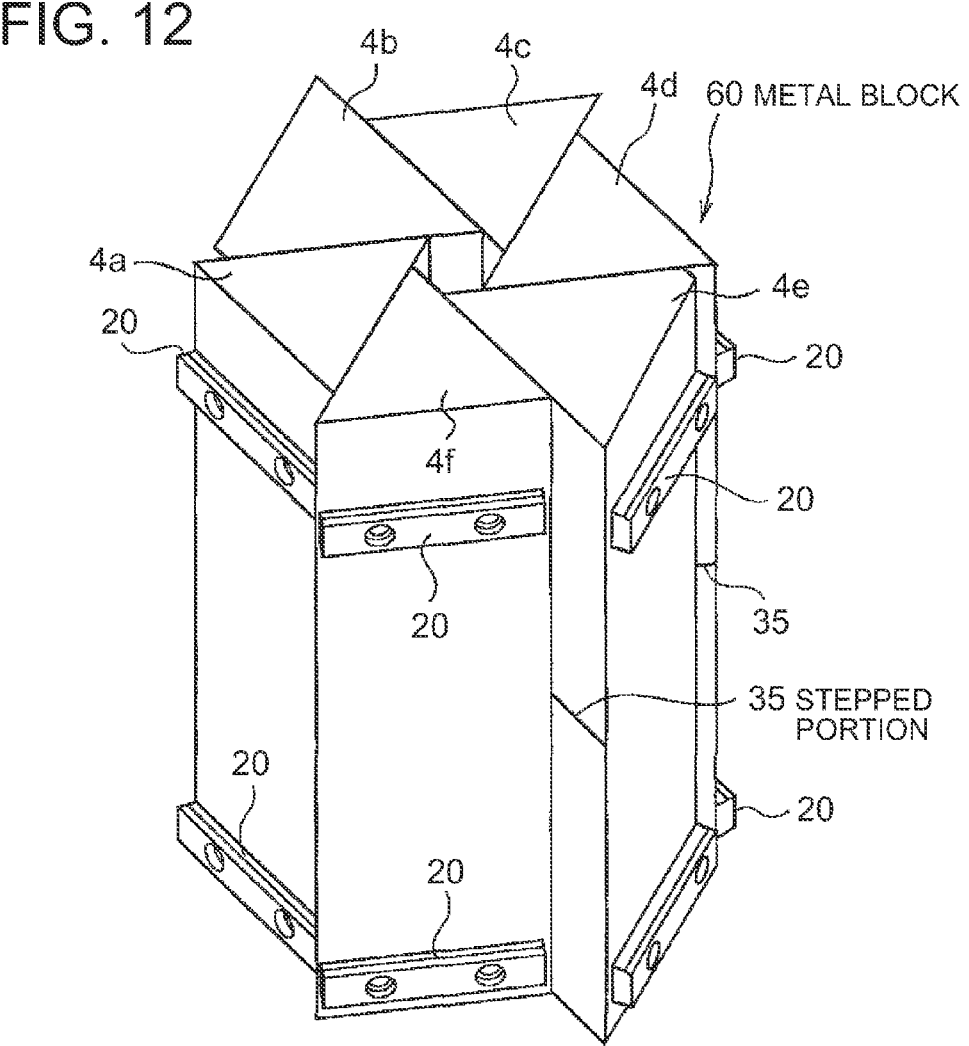
FIG. 12 is a perspective view of a metal block.

In addition, as shown in FIG. 12, the triangular prism members 4a to 4f are each provided with a stepped portion 35 in the vertical direction. The stepped portion 35 is provided at mutually facing vertically long rectangular surfaces of adjacent triangular prism members 4. FIG. 10 schematically illustrates, as an example, a stepped portion 35 provided at mutually facing surfaces of the triangular prism members 4d and 4e. A gap on the order of 0.1 mm is provided between the triangular prism members 4 (4a to 4f) from necessity of moving. Therefore, in order to prevent X-ray leakage from this gap, the stepped portion 35 of Δx in width is provided in the horizontal direction. For example, it has been confirmed that when the triangle shapes of triangular prism members 4 in planar view are dimensioned to have a side of 30 mm in length, the prevention of X-ray leakage can be achieved favorably with Δx=0.2 mm.

Figure 5A:
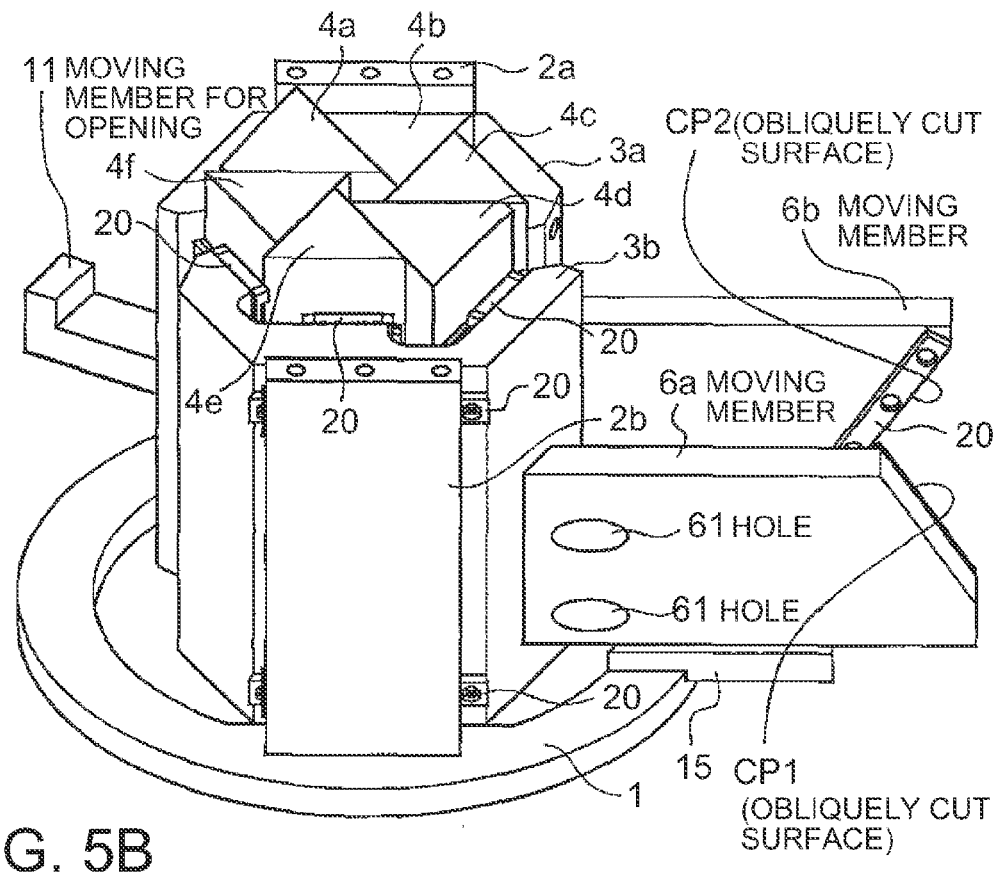
FIGS. 5A and 5B are respectively a perspective view and a plan view of the structure mounted with moving members and a moving member for opening and closing.
Figure 5B:
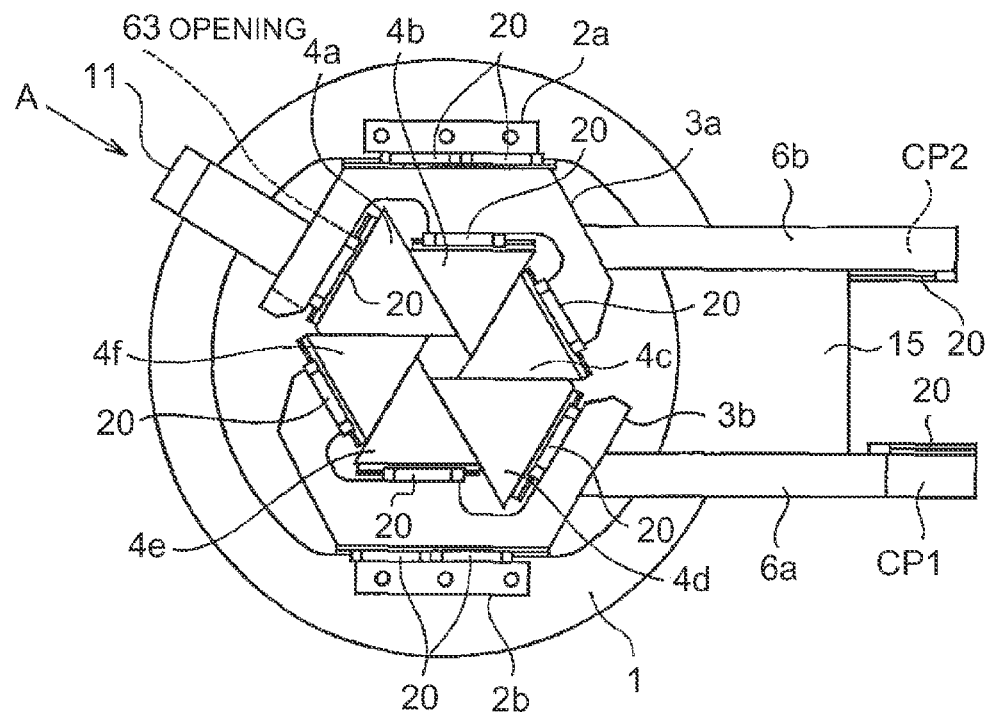

Next, the structure in FIGS. 4A and 4B, mounting moving members 6a and 6b and a moving member 11 for opening and closing will be described with reference to FIGS. 5A and 5B. FIG. 5A is a perspective view, whereas FIG. 5B is a plan view. The moving members 6a and 6b are respectively members which are horizontally moved parallel to the opposed surfaces of the regulating members 2a and 2b, and fixed in place with screws through two holes 61 arranged in the vertical direction and the holes 62 shown in FIG. 4, etc., to the external surfaces (outside wall surfaces) on the back of the apparatus (the right-hand side in the figure) among the respective U-shaped three wall surfaces of the surrounding member 3a and 3b. It is to be noted that the screwed section of the moving member 6b is not visible in the views shown in FIGS. 5A and 5B.

The moving member 6a has a substantially rectangular shape in side view, and has an upper back end cut obliquely as an obliquely cut section, with an obliquely cut surface CP1 formed. Along this obliquely cut surface (CP1), a linear slide 20 is provided on the inside of the moving member 6a (on the side with the opposed surfaces of both the moving members 6a and 6b). Furthermore, the moving member 6b also has a substantially rectangular shape in side view, and has an obliquely cut back end formed as an obliquely cut section, thus with an obliquely cut surface CP2 formed (in particular, see FIG. 5A). A linear slide 20 is provided along this obliquely cut surface CP2. As viewed from the side of the apparatus, the oblique direction of the obliquely cut surface CP1 of the moving member 6a crosses the oblique direction of the obliquely cut surface CP2 of the moving member 6b.

More specifically, as can be seen with reference to FIG. 5A, the oblique direction (direction of tilt) of the obliquely cut surface CP1 of the moving member 6a is "downward-sloping" as viewed from the near side of the apparatus, and a direction of sloping toward the near side as viewed from the back of the apparatus (see FIG. 15 described later). On the other hand, the oblique direction (direction of tilt) of the obliquely cut surface CP2 (see FIGS. 5 and 15) of the moving member 6b is "upward-sloping" as viewed from the near side of the apparatus, and a direction of sloping toward the far side as viewed from the back of the apparatus (see FIG. 15). Accordingly, when both of the cut surfaces CP1 and CP2 are viewed from the side of the apparatus, the oblique directions cross each other. Furthermore, the linear slides 20 are provided respectively on the insides of both obliquely cut surfaces CP1 and CP2 along the oblique directions of both obliquely cut surfaces CP1 and CP2.

Figure 13A:
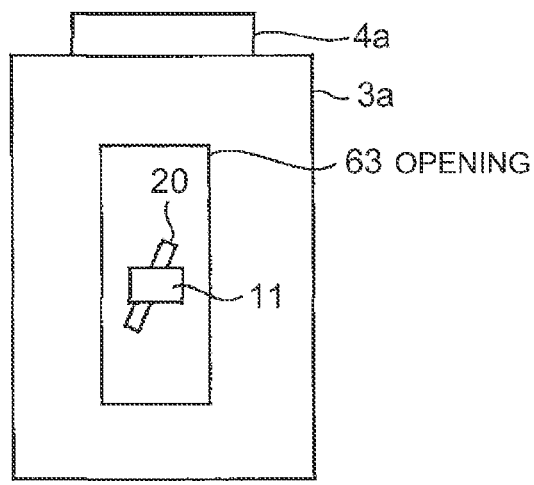
FIGS. 13A and 13B are respectively diagrams schematically illustrating the appearance of the moving member for opening, and a partial appearance of a structure mounted with the member.
Figure 13B:
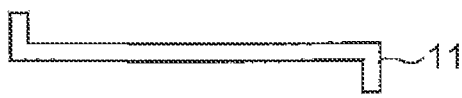

In addition, the moving member 11 for opening, which is a member extending to the outside of the apparatus and rectangular in planar view with a front end convex upwardly in the vertical direction, has a linear slide 20 mounted in an oblique direction on the front end and opposite end of the moving member 11. Furthermore, this linear slide 20 is coupled to a linear slide 20 provided in an oblique direction on the vertical long rectangular surface of the triangular prism member 4a through a vertically long opening 63 (see FIG. 13A) provided on the wall surface of the surrounding member 3a on the front of the apparatus (the left-hand side in the figure). FIG. 13B is a general side view of the moving member 11 for opening, whereas FIG. 13A is a schematic view as viewed from the direction of arrow indicated by a symbol A in FIG. 5B. It is to be noted that FIG. 13A is intended to schematically illustrate the relationship between the moving member 11 for opening and the triangular prism member 4a, and schematically illustrates only a relevant portion of the apparatus.

The moving member 11 for opening is composed of a columnar section extending horizontally, a section facing upward in the vertical direction at one end of the columnar section, and a section facing downward vertically at the other end thereof. Furthermore, the section facing upward vertically at the end is projected toward the outside of the apparatus as shown in FIG. 5A. Moreover, as shown in FIG. 13A, the section facing downward vertically at the other end is coupled by the linear slide 20 extending diagonally in an upward-sloping direction, through the vertically long opening 63 provided on the wall surface on the front of the apparatus 100 among the three wall surfaces of the surrounding member 3a, to the vertically long rectangular surface of the triangular prism member 4a, which faces toward the outside of the apparatus. Accordingly, the triangular prism member 4a is moved leftward in the figure (FIG. 13A) when the moving member 11 for opening is moved vertically upward (in an upward direction in the figure), whereas the triangular prism member 4a is moved rightward in the figure (FIG. 13A) when the moving member 11 for opening is moved vertically downward (in a downward direction in FIG. 13A).

Figure 6:
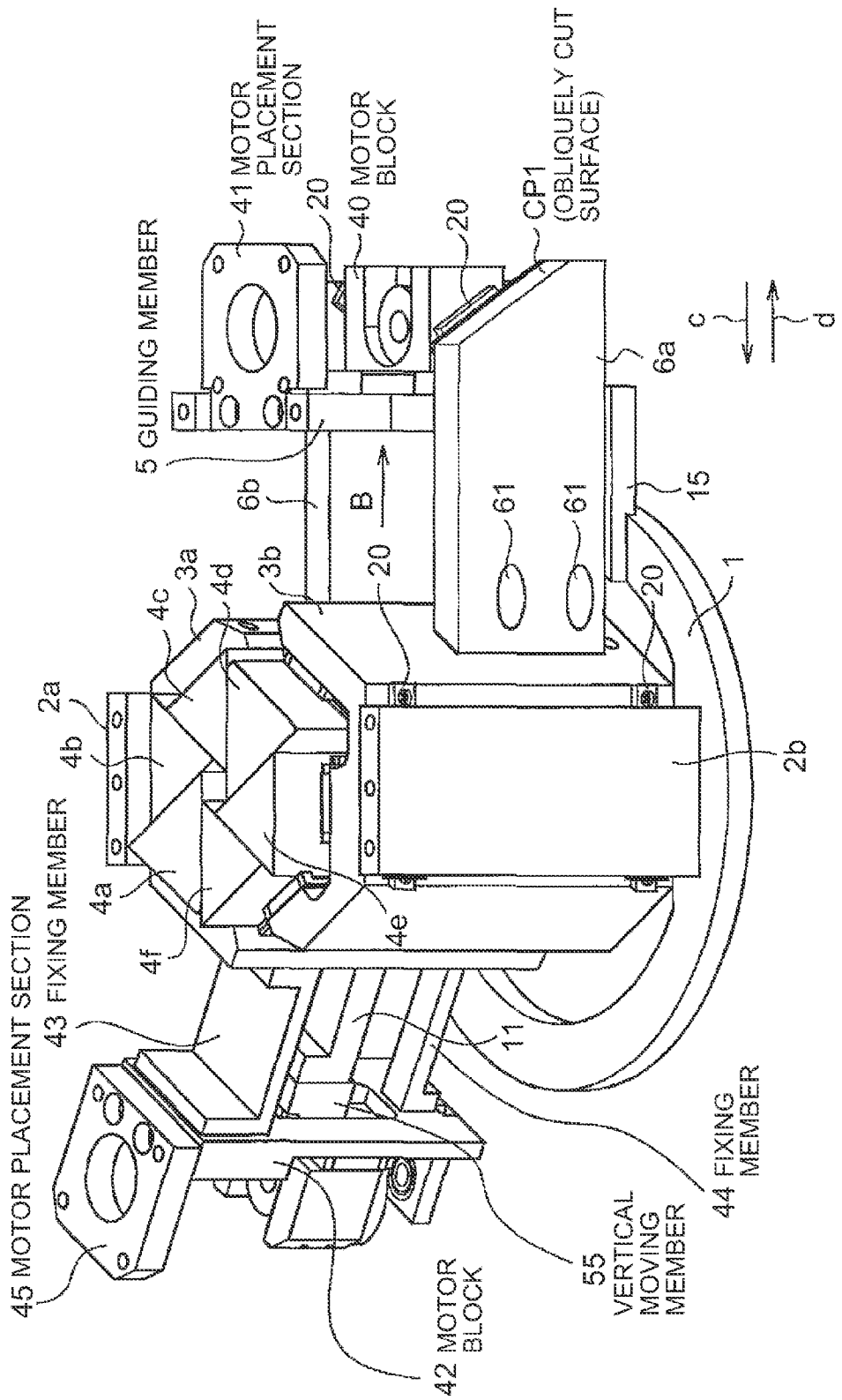
FIG. 6 is a perspective view of the structure mounted with a guiding member and motor blocks.
Figure 11:
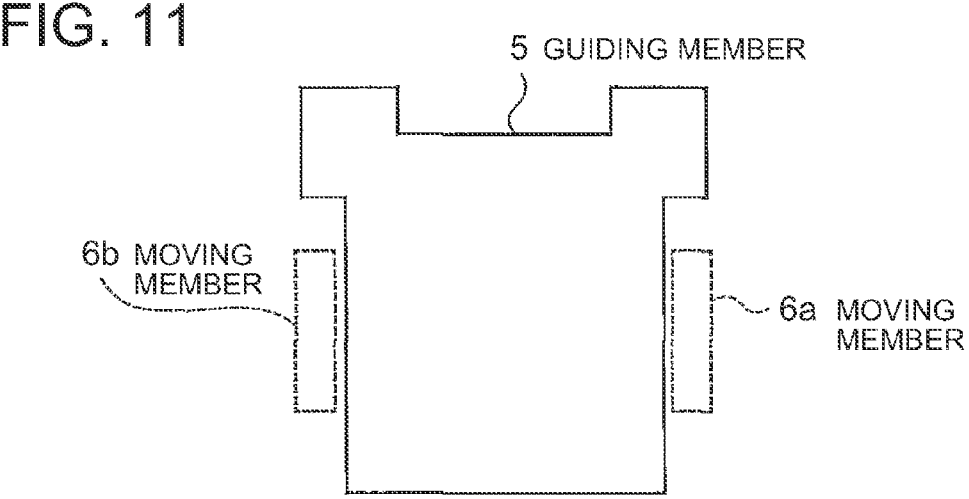
FIG. 11 is a schematic front view of the guiding member.

FIG. 6 is a perspective view of the structure in FIGS. 5A and 5B, mounting a guiding member 5, a motor block 40, another motor block 42, etc. The protruding section 15 extending outwardly from the lower base member 1 is provided vertically with the guiding member 5 orthogonal to the protruding direction. The view of the guiding member 5 from the direction of a symbol B in FIG. 6 is as shown in FIG. 11. As viewed from the direction of the symbol B, the guiding member 5, which is generally a vertically long rectangular member, has a concave upper end, and also right and left ends in such a shape missing, from the generally vertically-long rectangle, vertically-long sections from vertically somewhat upper-middle positions to the lower end.

Thus, the moving members 6a and 6b are movable in the vertical direction in the figure (FIG. 11), in such a manner that follows the right and left side surfaces. When the moving member 6a is moved to the near side of the figure (FIG. 11) in such a manner that follows the right side surface of the guiding member 5 in the figure (FIG. 11), the moving member 6b is moved to the far side of the figure (FIG. 11) in such a manner that follows the left side surface of the guiding member 5 in the figure (FIG. 11). Conversely, when the moving member 6a is moved to the far side of the figure (FIG. 11) in such a manner that follows the right side surface of the guiding member 5 in the figure (FIG. 11), the moving member 6b is moved to the near side of the figure (FIG. 11) in such a manner that follows the left side surface of the guiding member 5 in the figure (FIG. 11).

The moving member 6a and the moving member 6b are adapted to move horizontally in opposite directions, and move horizontally over the same distance. More specifically, referring to arrows indicated by a symbol c and a symbol d in FIG. 6, when the moving member 6a is moved horizontally in the direction of the arrow indicated by the symbol c, the moving member 6b is moved horizontally over the same distance in the opposite direction of the arrow indicated by the symbol d. Conversely, when the moving member 6a is moved horizontally in the direction of the arrow indicated by the symbol d, the moving member 6b is moved horizontally over the same distance in the opposite direction of the arrow indicated by the symbol c. It is to be noted that the moving mechanism will be described later.

Returning to FIG. 6 for further explanation, the motor block 40 on the right-hand side of the figure includes a motor placement section 41 provided on the uppermost surface of the motor block 40. Further, the motor placement section 41 is fastened with screws to a concave section of the upper end of the guiding member 5 to fix the motor block 40 entirely. In addition, as shown on the left-hand side in the figure, a motor block 42 provided with, on the top thereof, a motor placement section 45, is fixed by fastening a fixing member 43 and a fixing member 44 with screws to the wall surface on the front of the apparatus (the left-hand side in the figure), which is one of the three wall surfaces of the surrounding member 3a.

In addition, the front end of the moving member 11 for opening is coupled to a vertical moving member 55 to be movable up and down. Furthermore, the moving member 6a is, on the inside of the obliquely cut section described previously, provided with the linear slide 20 extending in the oblique direction. Likewise, the moving member 6b is, on the inside of the obliquely cut section, similarly provided with the linear slide 20 extending in the oblique direction. It is to be noted that, as described previously, the oblique direction corresponding to the extending direction of the linear slide 20 provided on the moving member 6a crosses the oblique direction corresponding to the extending direction of the linear slide 20 provided on the moving member 6b, as viewed from the side of the apparatus.

Figure 7:
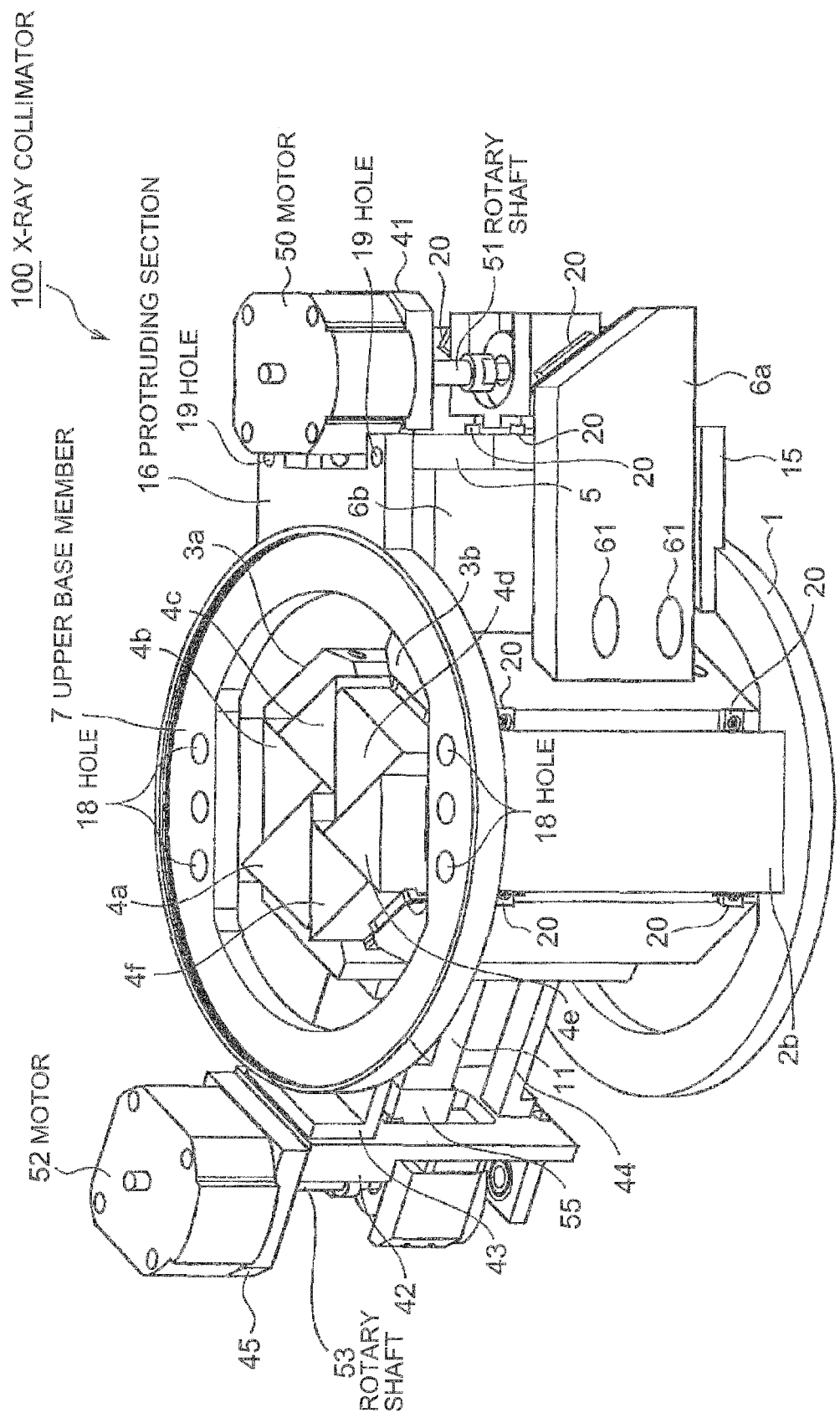
FIG. 7 is a perspective view of an X-ray collimator.
Figure 8:
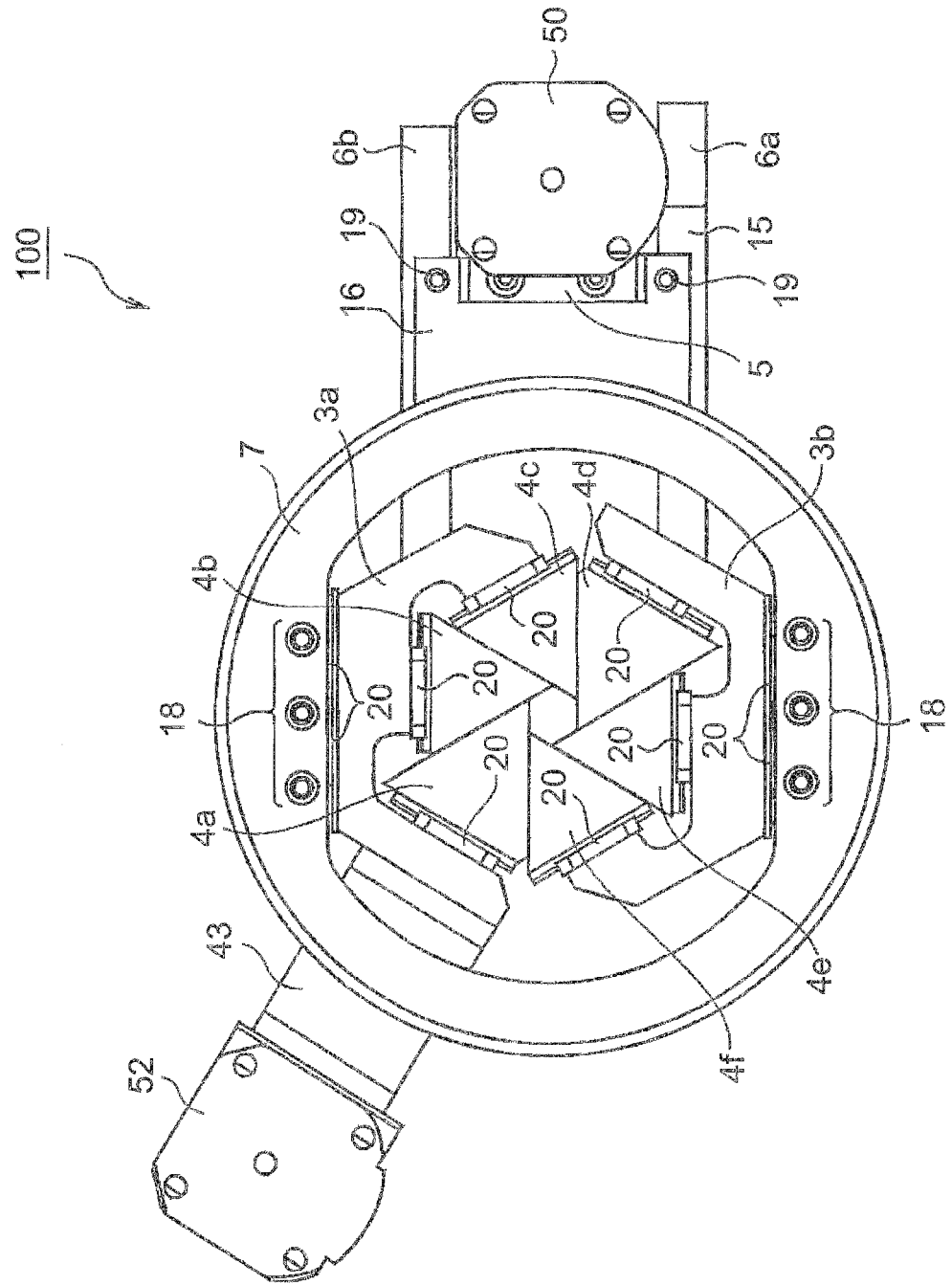
FIG. 8 is a plan view of the X-ray collimator.

Next, the structure in FIG. 6, mounting the motor 50, the motor 52, and an upper base member 7, will be described. FIG. 7 is a perspective view, and FIG. 8 is a plan view. The motor 50 with a rotary shaft 51 extending downward vertically is placed on the motor placement section 41, and the motor 50 is fastened in place with screws from the underside of the motor placement section 41. Likewise, the motor 52 with a rotary shaft 53 extending downward vertically is placed on the motor placement section 45, and the motor 52 is fastened in place with screws from the underside of the motor placement section 45. Furthermore, the annular section of the upper base member 7 has rows of three horizontal holes 18 formed with a substantially elliptical hollow interposed therebetween, so that six holes 18 in total are formed.

The upper base member 7 is fastened in place with screws through the six screw holes 18 in total, and through the holes formed in the upper surfaces of the regulating members 2a and 2b. The upper base member 7 is a substantially annular member in planar view, and this annular shape has therein the hollow formed in a substantially elliptical planar shape. A protruding section 16 extending from a portion of the outer edge of the annular section of the upper base member 7 toward the back of the apparatus (the right-hand side in the figure), is configured integrally therewith and, in the present embodiment, is manufactured from aluminum. Furthermore, the protruding section 16 has a pair of holes 19 formed at the end on the right-hand side in the figure, and in positions near the right and left ends in a planar view. The upper base member 7 is fixed by screwing through these holes 19 into a pair of right and left holes provided in the upper surface of the guiding member 5.

In sum, as described above, the X-ray collimator 100 includes: the pair of regulating members 2a and 2b provided vertically on the lower base member 1, so as to have their opposed surfaces parallel to each other; the pair of surrounding members 3a and 3b sandwiched between the opposed surfaces of the regulating members 2a and 2b, in such a way that both U-shaped forms face each other; the six triangular prism members 4a to 4f surrounded by the pair of surrounding members 3a and 3b; and the guiding member 5 provided vertically on the protruding section 15 extending from a portion of the outer edge of the lower base member 1, which has a rectangular shape in planar view so that the longitudinal direction of the rectangle is perpendicular to the opposed surfaces of the regulating members 2a and 2b.

Further, the X-ray collimator 100 includes: the moving members 6a and 6b as a pair of members, which are moved parallel to the opposed surfaces of the regulating members 2a and 2b in a manner that follows both the respective side surfaces of the guiding members 5, and fixed on the outside wall surfaces near the guiding member 5 among the three wall surfaces for each of the surrounding members 3a and 3b; and the upper base member 7 for fixing the upper surfaces of the regulating members 2a and 2b and the upper surface of the guiding member 5.

(Electrical Driving Source and Moving Mechanism)

Figure 14:
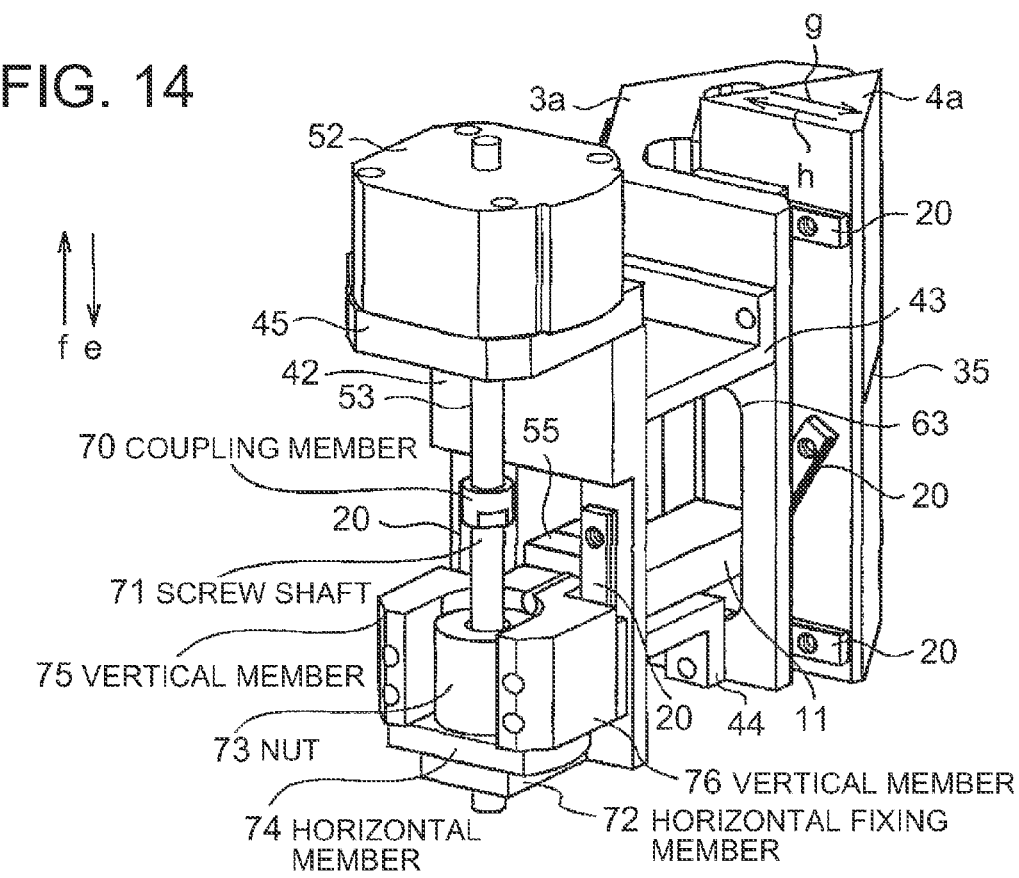
FIG. 14 is a diagram illustrating the appearance of a mechanism driven by a motor.

FIG. 14 is a diagram schematically illustrating a moving mechanism for driving the motor 52 (second electrical driving source) to move up and down the moving member 11 for opening, and as a result, moving the triangular prism member 4a along one of the three wall surfaces of the surrounding member 3a (the inside wall surface on the front of the apparatus (on the left-hand side in the figure): see reference symbol TW in FIG. 3B). FIG. 14 is a schematic diagram illustrating only a relevant portion of the apparatus for explaining the moving mechanism for the triangular prism member 4a. A ball screw is used to construct the moving mechanism for moving the triangular prism member 4a.

As shown in FIG. 14, the rotary shaft 53 of the motor 52 is coupled through a coupling member 70 to a screw shaft 71 (for the ball screw) extending vertically. The screw shaft 71 has a cylindrical nut 73 screwed thereon. Further, the lower end of the screw shaft 71 is supported, via a bearing, on the inner surface of a circular hole formed substantially in the center of a horizontal fixing member 72, which is a member in the form of a rectangular plate in appearance, and fixed by screwing into the motor block 42. In addition, the nut 73 is fixed on a horizontal member 74, and a pair of vertical members 75 and 76 is fixed on right and left ends of the horizontal member 74.

Furthermore, the pair of vertical members 75 and 76 is coupled to the motor block 42 respectively through a pair of linear slides 20 extending vertically. Thus, when the screw shaft 71 is rotated, the nut 73 moves up and down, thereby also moving the section composed of the horizontal member 74 and the pair of vertical members 75 and 76. It is to be noted that FIG. 14 shows the nut 73 located in the lowest position in the vertical direction.

When the rotary shaft 53 of the motor 52 is rotated in the normal direction (for example, clockwise), the screw shaft 71 is rotated via the coupling member 70 to move the nut 73 downward (see an arrow with reference symbol e), thereby also moving downward the horizontal member 74 and the pair of vertical members 75 and 76. Thus, the vertical moving member 55 fixed on the pair of vertical members 75 and 76 also moves downward. As a result, the moving member 11 for opening, which is fixed on the vertical moving member 55, is moved downward, and the triangular prism member 4a is thus moved in the direction of arrow indicated by reference symbol g via the linear slide 20 provided obliquely on the vertically long surface of the triangular prism member 4a. Conversely, when the rotary shaft 53 of the motor 52 is rotated in the reverse direction, the nut 73 is in turn moved upward (see an arrow with reference symbol f), and the triangular prism member 4a is eventually moved in the direction indicated by reference symbol h. Accordingly, the upward and downward movements (see the arrows with the reference symbols e and f) of the nut 73 via the normal rotation and reverse rotation of the motor 52 translate to the horizontal movements (see the arrows with the symbols g and h) of the triangular prism member 4a.

Figure 16A:
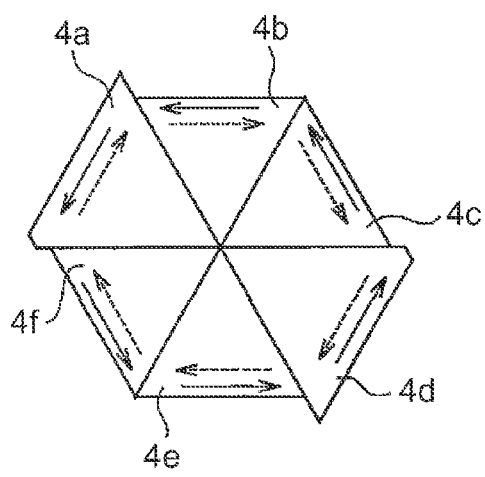
FIGS. 16A and 16B are diagrams schematically illustrating moving directions of the triangular prism members.

Thus, when one of the triangular prism members (the member 4a) is moved, the other triangular prism members 4b to 4f coupled with the linear slides 20 of the surrounding members 3a and 3b are then sequentially moved horizontally along the linear slides 20. FIG. 16A is a schematic plane view illustrating the respective triangular prism members 4a to 4f moved by the rotation of the motor 52. The respective triangular prism members 4a to 4f are horizontally moved as indicated by solid arrows by the normal rotation of the rotary shaft 53 of the motor 52, and horizontally moved as indicated by dotted arrows by the reverse rotation thereof.

Figure 15:
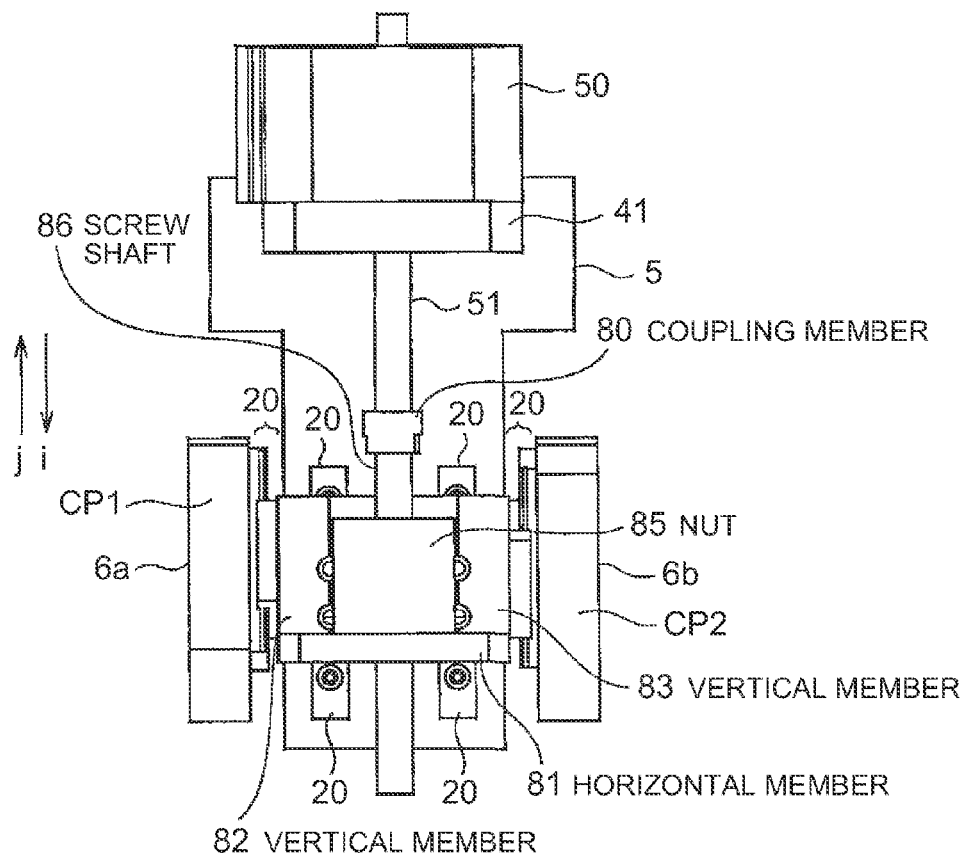
FIG. 15 is a diagram illustrating the appearance of a mechanism driven by another motor.

Next, FIG. 15 is a diagram schematically illustrating a moving mechanism for driving the motor (first electrical driving source) to move the moving members 6a and 6b over the same distance in horizontally opposite directions (directions vertical to plane of paper). FIG. 15 is a schematic diagram illustrating a relevant portion of the apparatus for explaining the moving mechanism for the moving members 6a and 6b. The moving mechanism also constructs the moving mechanism for moving the moving members 6a and 6b.

As shown in FIG. 15, the rotary shaft 51 of the motor 50 placed and fixed on the motor placement section 41 is coupled through a coupling member 80 to a screw shaft 86 (for the ball screw) extending vertically. The screw shaft 86 has a cylindrical nut 85 screwed thereon. In addition, the nut 85 is fixed on a horizontal member 81, and a pair of vertical members 82 and 83 is fixed on right and left ends of the horizontal member 81. Furthermore, the pair of vertical members 82 and 83 is coupled to the guiding member 5 respectively via linear slides 20 extending vertically.

Thus, when the screw shaft 86 is rotated, the nut 85 moves up and down, thereby also moving up and down the section composed of the horizontal member 81 and the pair of vertical members 82 and 83. In addition, the vertical member 82 is coupled to the moving member 6a via a linear slide 20, whereas the vertical member 83 is also coupled to the moving member 6b via a linear slide 20. It is to be noted that, as described above, the linear slide 20 is provided so as to extend in the oblique direction of the obliquely cut surface CP1 of the moving member 6a, and the linear guide 20 couples the vertical member 82 and the moving member 6a to each other. Likewise, the other linear slide 20 is provided so as to extend in the oblique direction of the obliquely cut surface CP2 of the moving member 6b, and the linear guide 20 couples the vertical member 83 and the moving member 6b to each other. It is to be noted that, as described previously, referring to FIG. 15, the obliquely cut surface CP1 of the moving member 6a is tilted to the front of the drawing, whereas the obliquely cut surface CP2 of the moving member 6b is tilted to the back of the drawing. Therefore, the directions of tilt (oblique directions) of both obliquely cut surfaces CP1 and CP2 cross each other as viewed from the side of the apparatus.

When the rotary shaft 51 of the motor 50 is rotated in the normal direction, the screw shaft 86 is rotated via the coupling member 80 to move the nut 85 downward (see an arrow with reference symbol i), thereby also moving downward the section composed of the horizontal member 81 and the pair of vertical members 82 and 83. As a result, the linear slide 20 coupling the vertical member 82 and the moving member 6a moves the moving member 6a in the perpendicular direction to the back of the figure, whereas the linear slide 20 coupling the vertical member 83 and the moving member 6b moves the moving member 6b in the perpendicular direction to the front of the figure (the moving member 6n is moved in the direction of arrow indicated by the reference symbol c in FIG. 6, whereas the moving member 6b is moved in the direction of arrow indicated by the reference symbol d in FIG. 6). These two moving members 6a and 6b move over the same distance.

Conversely, when the rotary shaft 51 of the motor 50 is rotated in the reverse direction, the nut 85 is in turn moved upward (see an arrow with reference symbol j), and the moving member 6a is moved in the perpendicular direction to the front of the figure, whereas the moving member 6b is moved in the perpendicular direction to the back of the figure, each horizontally over the same distance (the moving member 6a is moved in the direction of arrow indicated by the reference symbol d in FIG. 6, whereas the moving member 6b is moved in the direction of arrow indicated by the reference symbol c in FIG. 6). Thus, the moving member 6a and the moving member 6b are moved horizontally over the same distance in the directions opposite to each other in a manner that follows both side surfaces of the guiding member 5, so that the pair of surrounding members 3a and 3b is also moved horizontally over the same distance respectively in the opposite directions. As a result, the set of three triangular prism members 4a, 4b, 4c surrounded by the surrounding member 3a moves horizontally, whereas the set of three triangular prism members 4d, 4e, 4f surrounded by the surrounding member 3b also moves horizontally.

Figure 16B:
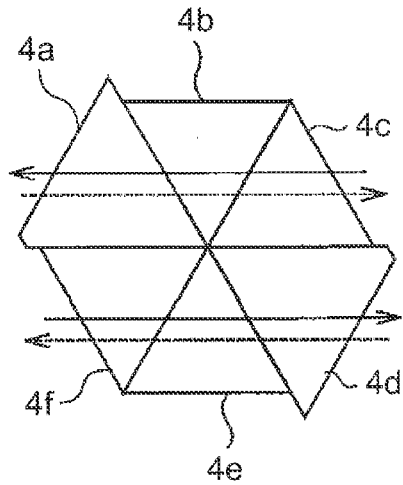

FIG. 16B is a schematic plane view illustrating the respective triangular prism members 4a to 4f moved by the rotation of the motor 50. The respective triangular prism members 4a to 4c and 4d to 4f are horizontally moved as indicated by solid arrows by the normal rotation of the rotary shaft 51 of the motor 50, and horizontally moved as indicated by dotted arrows by the reverse rotation thereof. In the way described above, the two motors 50 and 52 can move the triangular prism members 4a to 4f as in FIGS. 16A and 16B.

(Rotation of Apparatus)

Figure 26A:
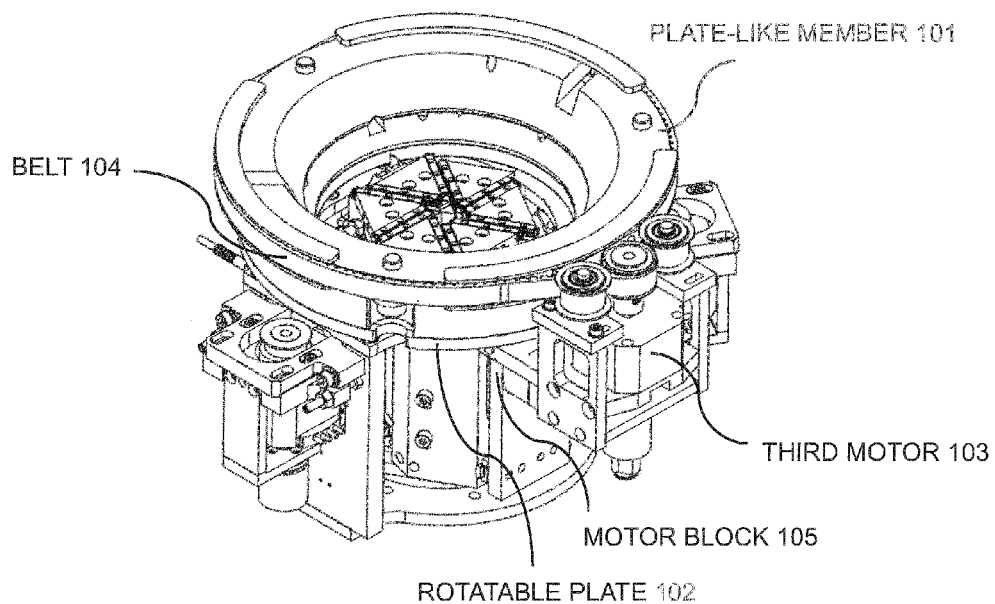
FIGS. 26A and 26B are diagrams showing perspective and side views, respectively, of a variation of the X-ray collimator, in which a third motor is attached to a motor block of the X-ray collimator.
Figure 26B:
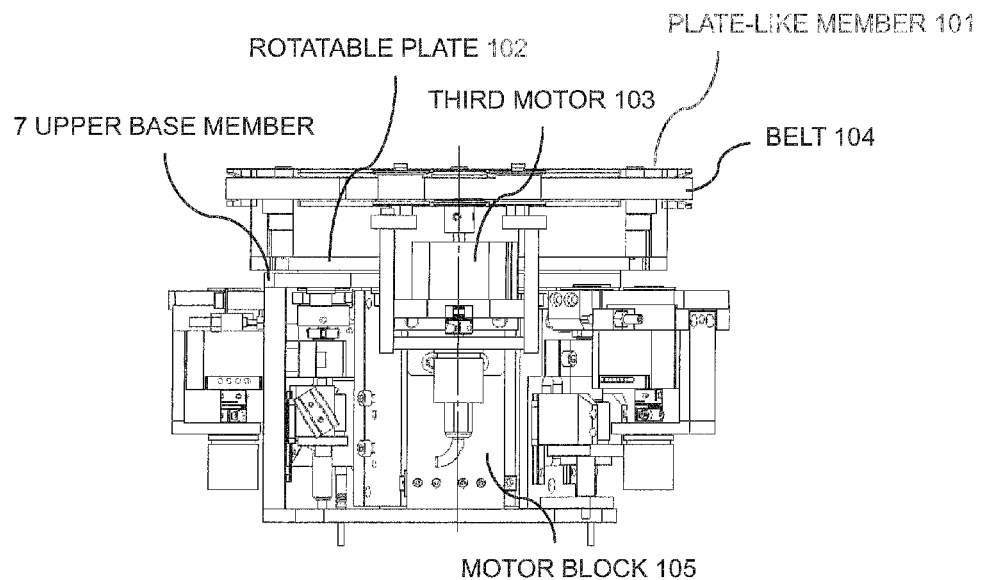

Rotating the X-ray collimator 100 itself can be also achieved by a known mechanism. As an example, a plate-like member 101 with a horizontal surface is prepared on the upper side of the apparatus, and a circular rotatable plate 102 and a third motor 103 are provided on the lower surface of the plate-like member 101. Further, when the upper base member 7 is configured to be fixed on the rotatable plate 102, with a belt 104 forming a bridge between the third motor 103 and the upper base member 7, the apparatus itself will be rotated by rotating the third motor 103. As shown in FIGS. 26A and 26B, the third motor 103 is fixedly mounted on a motor block 105 projecting from the apparatus, with the belt 104 entrained around the third motor 103 and circular rotatable plate 102. In this case, it will be further preferable for the work of attaching the apparatus if the third motor 103 is configured to be fixed on the motor block 105 extending outward from the apparatus itself, because the third motor 103 fixed on the present apparatus itself makes the apparatus itself rotatable. It is to be noted that this configuration example is given by way of example, and other embodiments can also make the apparatus itself rotatable. In short, it is possible to make the apparatus itself rotatable, thereby easily making it possible to make fine adjustments of the three-dimensional position of the X-ray collimator during X-ray irradiation for greater precision and ease of use.

(Operation)

Figure 17A:
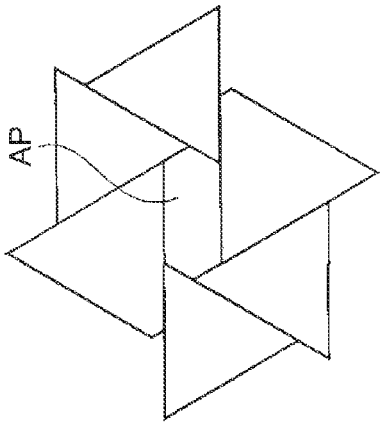
FIGS. 17A to 17F are diagrams schematically illustrating changes of an aperture.
Figure 17B:
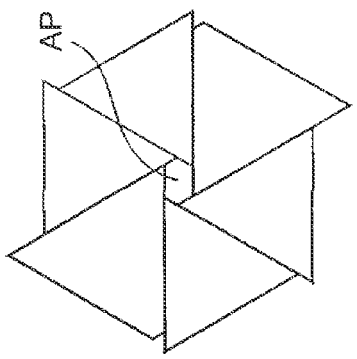
Figure 17C:
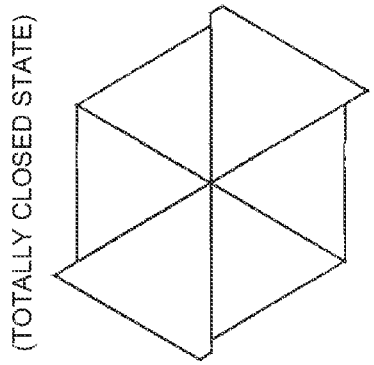

FIGS. 17A to 17F are schematic plan views illustrating how an aperture (AP) formed by the six triangular prism members 4a to 4f is changed by driving the two motor 50 (the electrical driving source for moving the moving members 6a and 6b) and motor 52 (the electrical driving source for moving the triangular prism member 4a). FIG. 17A shows the aperture closed completely before driving both motors 50 and 52 (totally closed state). When both the motors 50 and 52 are gradually rotated in the normal direction from this state, the aperture (AP) will take a hexagonal shape which is not a regular hexagon, but a horizontally elongated hexagon in the figure (see FIG. 17B). More specifically, this hexagonal shape is a horizontally long hole. Furthermore, when the motors 50 and 52 continue to be rotated in the normal direction, the aperture (AP) will take a hexagonal shape which is long both in the vertical direction of the drawing and in the horizontal direction of the drawing as shown in FIG. 17C, and the long hole will be thus increased in size.

Figure 17D:
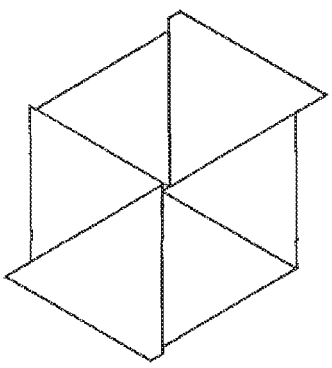
Figure 17E:
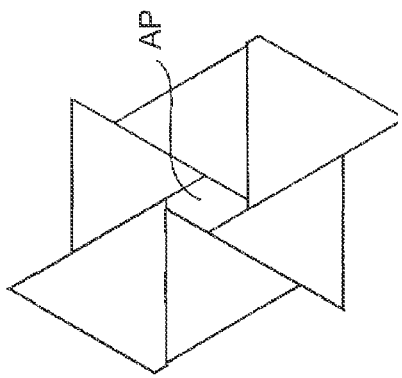
Figure 17F:
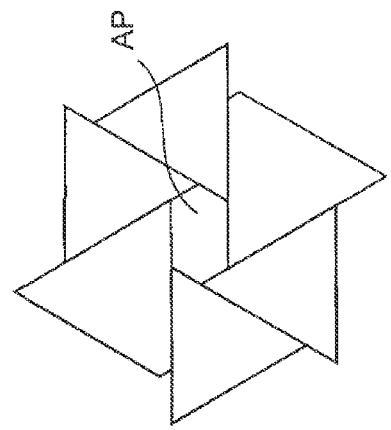

Next, in this state, when the motor 50 is in turn rotated in the reverse direction, the hexagonal shape of the aperture (AP) will be shorter in the horizontal direction of the drawing and longer in the vertical direction of the drawing (see FIG. 17d). Furthermore, when the reverse rotation of the motor 50 is continued, the shape will be in turn a hexagon which is long in the vertical direction of the drawing as shown in FIG. 17E. More specifically, a long hole will be formed which is long in the vertical direction of the drawing. As described above, the embodiment of the present invention allows a regular hexagon to be changed to form a long hole which is long both in the horizontal direction and vertical direction of the drawing. Then, when both the motors 50 and 52 are rotated in the reverse direction, the aperture (AP) will be again turned into the completely closed state (totally closed state).

As described above, the present embodiment differs from conventional simply circular apertures scaled up and down and the shapes of regular hexagonal apertures scaled up and down while maintaining the regular hexagonal shapes. According to the embodiment of the present invention, the use of the two motors, the motor 50 for horizontally moving the moving members 6a and 6b and the motor 52 for horizontally moving the triangular prism member 4a, can form a elongated opening quite similar to the shape of a general affected area to control the radiation field.

Therapeutic high-energy X-rays are reflected by the inner wall of the aperture (AP) of the collimator, then radiated, and transmitted through the end of the aperture of the collimator. A so-called penumbra is thus produced in the radiation field, and even healthy tissues around tumors are irradiated with the X-rays. In the case of treating small tumors of 1 cm or less in diameter or width, there is a need to reduce the X-ray beam diameter or width down to on the order of 1 mm in order to reduce the effect of the penumbra. Such a narrow X-ray beam is similarly effective for the edges of larger tumors as well. The X-ray collimator 100 according to the embodiment of the present invention can dynamically control the diameter or width of the radiation field in the range from 1 mm or less to approximately 30 mm when the triangle shapes of triangular prism members 4 in planar view are adapted to have a side of 30 mm in length, and is thus an X-ray collimator preferred for treating small tumors of 1 mm or less in diameter or width. It is to be noted that the control range of the radiation field diameter or width may be changed, and is not limited to the range mentioned above.

(Materials and Dimensions)

The materials and dimensions for the present apparatus will now be described.

Basically, each part of the present apparatus can be manufactured from aluminum. However, the metal block 60 composed of columnar members is manufactured from tungsten, and the nut 73, the nut 85, the screw shaft 71, the screw shaft 86, and the like are manufactured from stainless steel or the like. In addition, a prototype for the present apparatus is approximately 120 mm from the lower end of the lower base member 1 to the upper end of the upper base member 7, the annular sections of both base members are approximately 150 mm in diameter, and the apparatus is 212 mm in horizontal length and 156 mm in width, thus succeeding in achieving a quite-small X-ray collimator. It is to be noted that the materials and dimensions of the present invention are not limited to these.

Figure 18A:
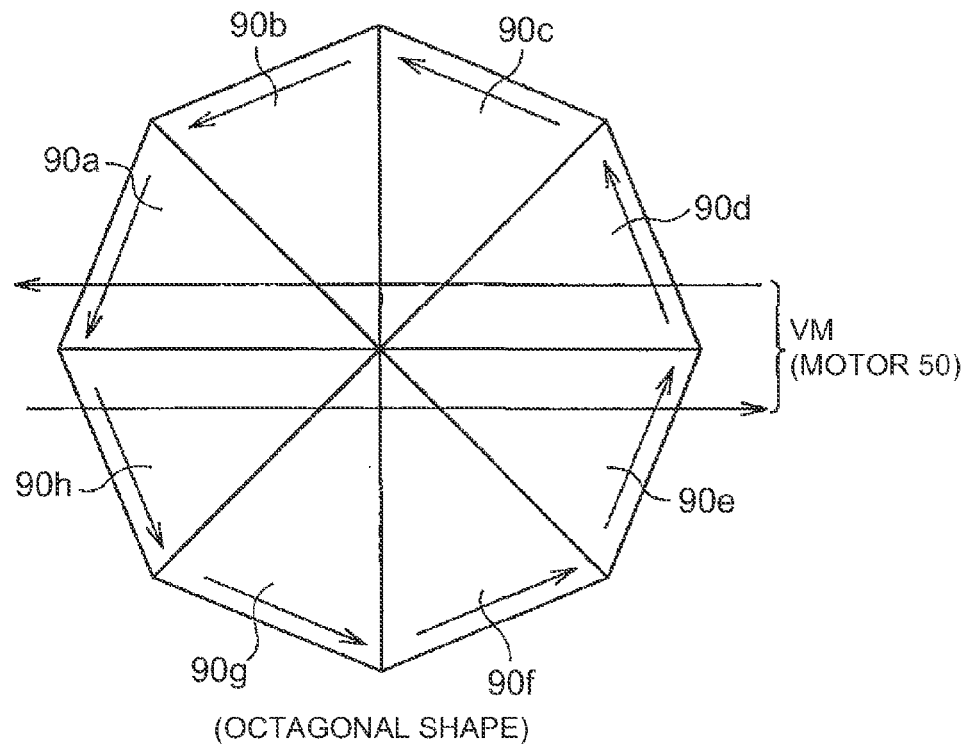
FIGS. 18A and 18B are diagrams schematically illustrating movements in other embodiments of the metal block.

Although the six triangular prism members 4a to 4f dividing the substantially hexagonal planar shape of the metal block 60 into six equal parts, which are surrounded by the pair of surrounding members 3a and 3b, have been described in the embodiment described above, the metal block 60 may have a planar shape other than the substantially rectangular hexagonal shape of the present embodiment. For example, even when eight triangular prism members dividing a substantially octagonal planar shape into eight equal parts are surrounded by a pair of surrounding members, the present apparatus can be configured with the elements other than the metal block 60 configured in the same way. FIG. 18A is a schematic plane view for explaining the movement of the metal block 60 in this case. Eight triangular prism members 90a to 90h dividing a regular octagonal shape into eight equal parts are moved in the horizontal direction of the figure by driving normal rotation of the motor 50 (see arrows with a symbol VM). The set of four triangular prism members (90a, 90b, 90c, 90d) surrounded by one of a pair of two surrounding members (not shown) each with four wall surfaces is moved together in the horizontal direction of the figure, whereas the other set of four triangular prism members (90e, 90f, 90g, 90h) surrounded by the other of the pair is moved together in the horizontal direction of the figure. In addition, when the triangular prism member 90a is moved in an oblique direction to the bottom left along the outer side of the member as shown in the figure by driving the motor 52, the other triangular prism members 90b to 90h are sequentially moved in conjunction with each other as indicated by arrows. Thus, the aperture is formed into a slot shape by driving the motors 50 and 52, as in the case of the metal block 60 in the substantially regular hexagonal planar shape. It is to be noted that in the case of the metal block 60 in the substantially regular octagonal planar shape, the respective triangular prism members 90a to 90h have planar shapes of isosceles triangles.

Figure 18B:
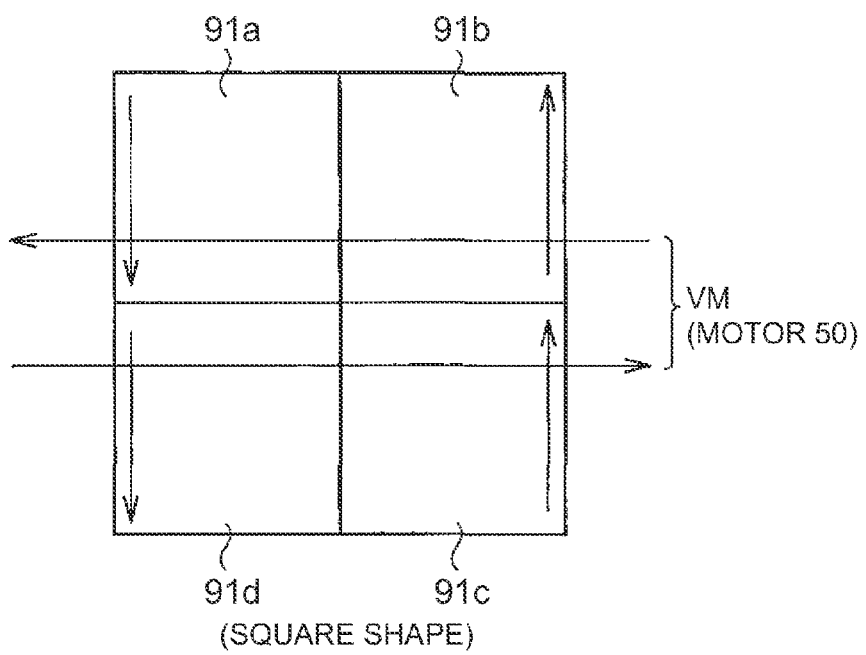
Figures 19A, 19B, 19C:
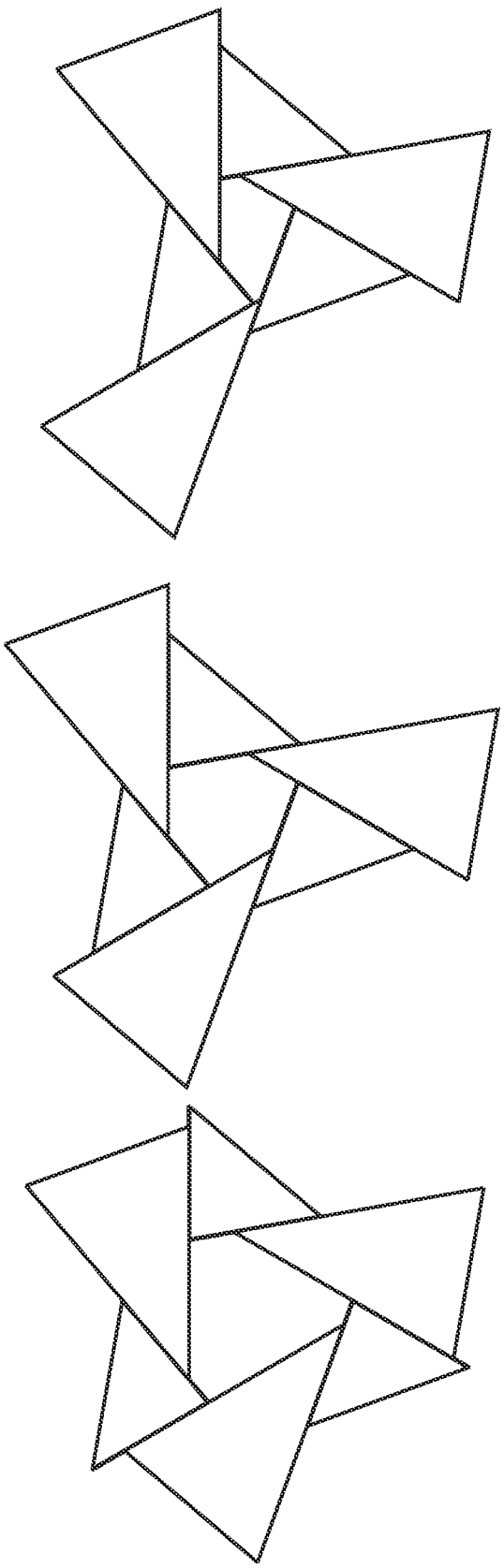
Figure 20C:
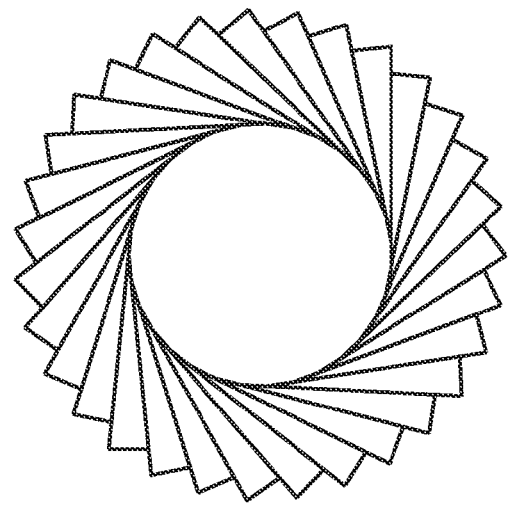
Figure 20B:
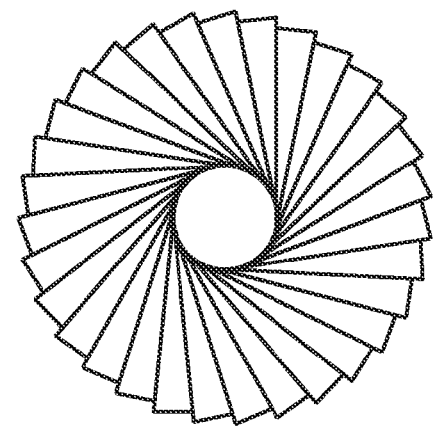
Figure 20A:
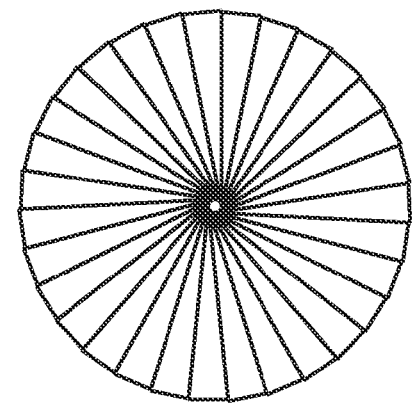
Figure 21A:
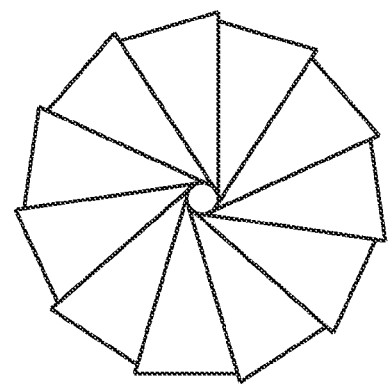
Figure 21B:
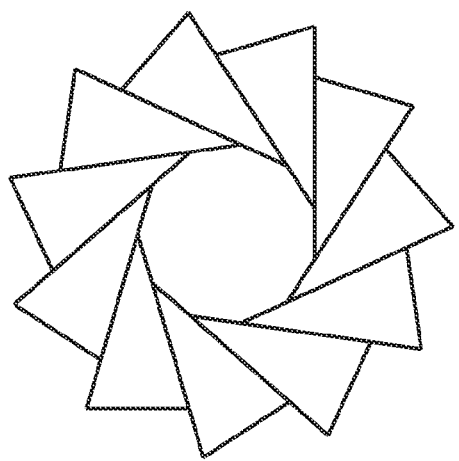
Figure 21C:
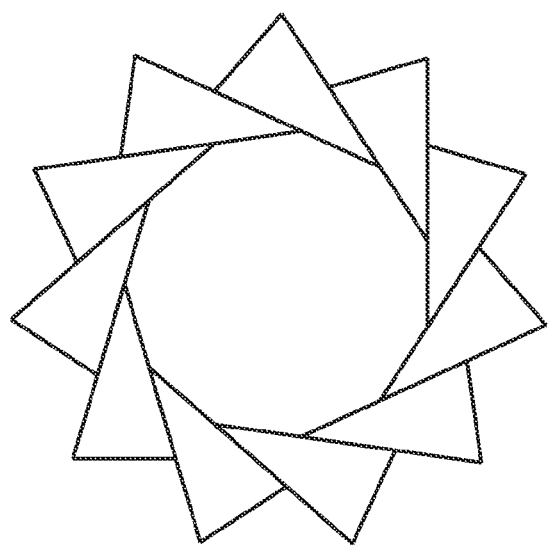
Figure 22A:
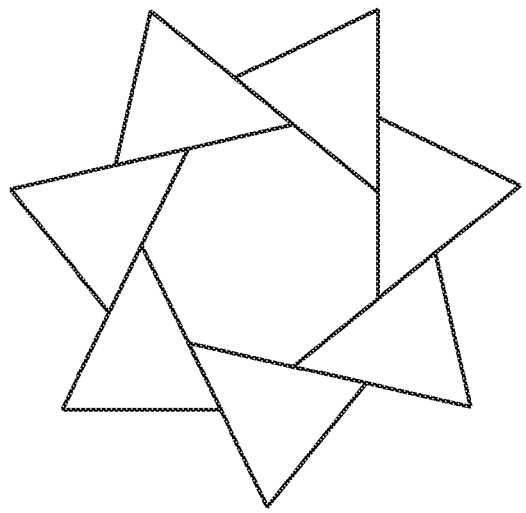
Figure 22B:
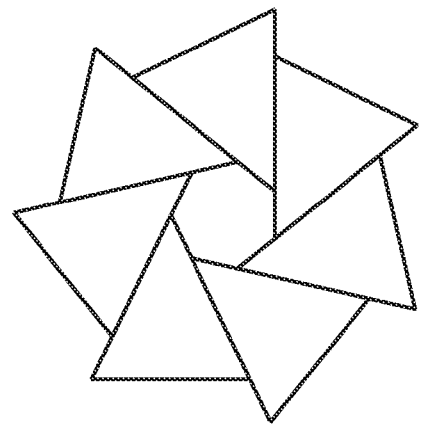
Figure 22C:
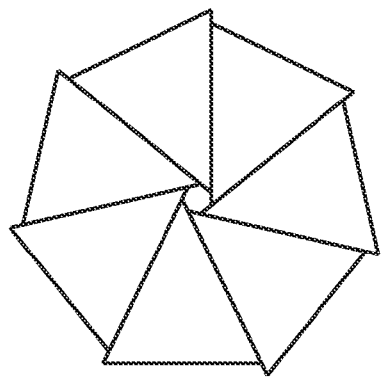
Figure 23C:
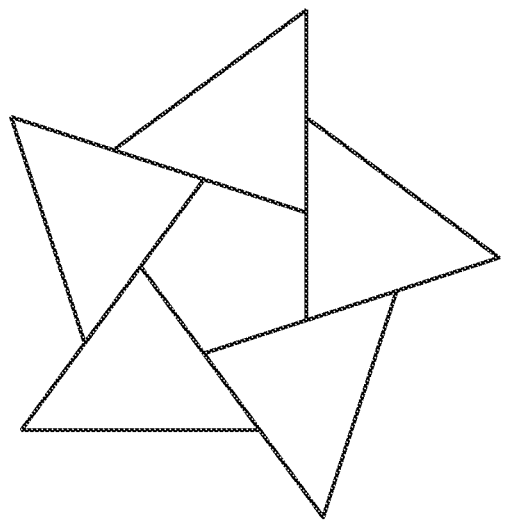
Figure 23B:
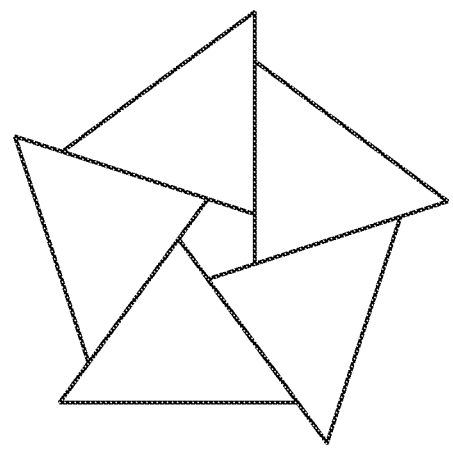
Figure 23A:
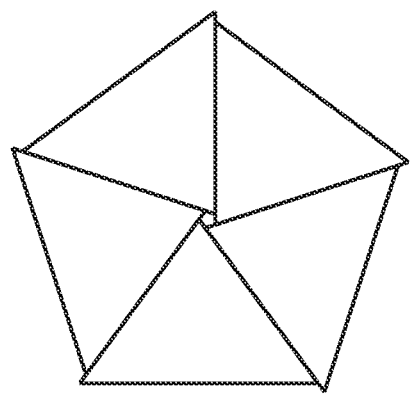
Figures 25A, 25B, 25C, 25D:
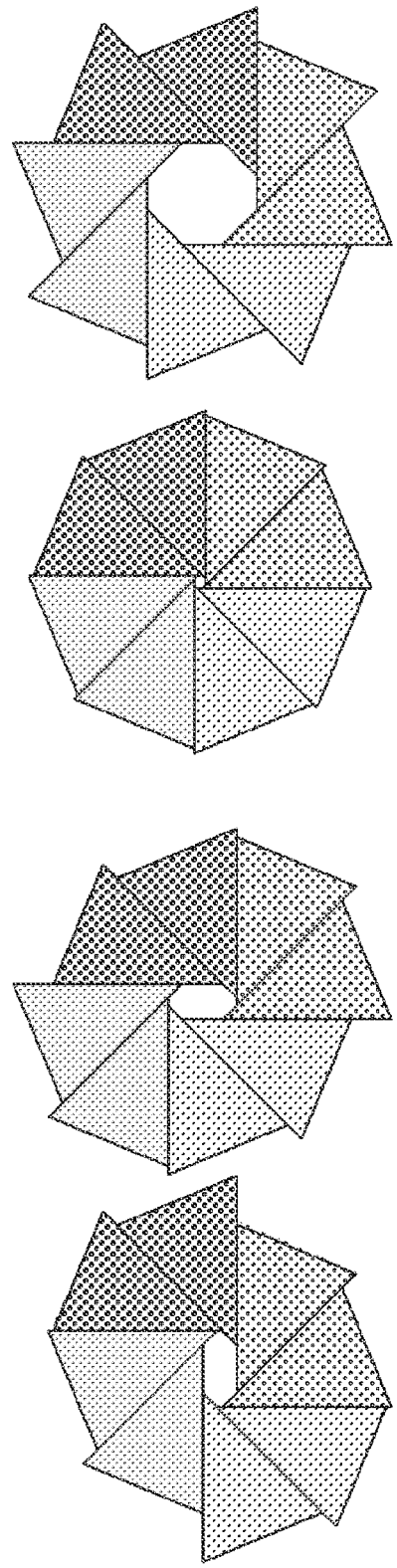

Likewise, in the case of the metal block 60 in a substantially regular square planar shape, four quadrangular prism members 91a to 91d dividing the regular square shape into four equal parts can be used to form a long hole as an aperture. FIG. 18B is a schematic plane view for explaining the movement of the metal block 60 in this case. Four quadrangular prism members 91a to 91d dividing a regular square shape into four equal parts are moved in the horizontal direction of the figure by driving normal rotation of the motor 50 (see arrows with a symbol VM). The set of two quadrangular prism members (91a, 91b) surrounded by one of a pair of surrounding members (not shown) is moved together in the horizontal direction of the figure, whereas the other set of two quadrangular prism members (91c, 91d) surrounded by the other of the pair is moved together in the horizontal direction of the figure. In addition, when the quadrangular prism member 91a is moved in a direction to the bottom of the figure along the outer side of the member as shown in the figure by driving the motor 52, the other quadrangular prism members 91b to 91d are sequentially moved in conjunction with each other as indicated by arrows. Thus, the aperture is formed into a slot shape by driving the motors 50 and 52, as in the case of the metal block 60 in the substantially regular hexagonal planar shape. It is to be noted that the facing surfaces of the quadrangular prism member 91d and quadrangular prism member 91c, as well as the facing surfaces of the quadrangular prism member 91a and quadrangular prism member 91b, are coupled via linear slides which are tilted at an angle of 45 degrees, and it thus becomes possible to achieve the movements of the quadrangular prism members 91c and 91b in a direction to the top of the figure with respect to the movements of the quadrangular prism members 91d and 91a in a direction to the bottom of the figure. In this way, the planar shape of the metal block 60 may be not only a substantially regular hexagonal, but also a substantially regular octagonal and a substantially regular square.

When the planar shape of the metal block 60 is a substantially regular square, hexagonal, or octagonal (a substantially regular polygon shape, where N=4, 6, or 8) as described above, the same advantageous effect can be achieved even in the case of using columnar members (specifically, triangular prism members, quadrangular prism members) each dividing the planar shape into four, six, or eight parts. In addition, even when the planar shape does not always have an even number of sides (for example, a substantially regular triangle, substantially regular pentagon, substantially regular heptagon, or the like), the same advantageous effect can be produced in theory by appropriately changing the shape of the inner wall surfaces of the two surrounding members.

As described above, the X-ray collimator 100 according to the embodiment of the present invention can form the aperture into a slot shape at least in two directions. As a result, the X-ray collimator has advantages such as that it becomes possible to carry out X-ray therapy for slot-shaped affected areas a reduced number of times. Moreover, the X-ray collimator can prevent the X-ray leakage other than from the X-ray aperture, and the apparatus itself can also rotate. Thus, an X-ray collimator can be achieved which has further improved usability as compared with conventional X-ray collimators, and the use of the thin long hole also makes it possible to deal with X-ray therapy for small tumors of 1 cm or less, which have not been able to be treated conventionally. Further, the aperture of the collimator is changed in shape and direction dynamically by driving the motors 50 and 52, thereby allowing for X-ray therapy with swiftness and accuracy even for affected areas in complex shapes.

The X-ray collimator according to the present invention is widely applicable to radiation therapy apparatuses for carrying out radiation therapy in the medical field.

Numerous additional modifications and variations of the above-described embodiment are possible in light of the above teachings. It is therefore to be understood that, within the scope of the appended claims, the disclosure of the present invention may be practiced otherwise than as specifically described herein. For example, elements and/or features of different examples and illustrative embodiments may be combined each other and/or substituted for each other within the scope of this disclosure and the appended claims. In particular, the number and shape of the triangular prism members can be varied considerably, as illustrated in FIGS. 19A through 25D, which are diagrams schematically illustrating other embodiments of the triangular prism members and their associated movements and illustrating the changes in the size and shape of the apertures formed thereby.

What is claimed is:

1. An X-ray collimator for controlling an X-ray radiation field, the X-ray collimator comprising:
a lower base member to serve as a base for the X-ray collimator and comprising a protruding section;
a pair of regulating members provided vertically on the lower base member, so as to have opposed surfaces parallel to each other;
a pair of surrounding members each having a substantially U-shaped form in planar view and having a predetermined height, each of the pair of surrounding members sandwiched between the opposed surfaces of the pair of regulating members in such a way that both U-shaped forms face each other;
N columnar members surrounded by the pair of surrounding members, each of the N columnar members having a planar shape obtained by dividing a substantially regular polygon shape into N equal parts, where N is 4, 6, or 8;
a guiding member having a rectangular shape in planar view, provided vertically on the protruding section extending from the lower base member so that the rectangular shape has a long side perpendicular to the opposed surfaces of the pair of regulating members;
a pair of moving members configured to move parallel to the opposed surfaces of the pair of regulating members in a manner that respectively follows both respective side surfaces of the guiding member, and fixed on external surfaces of each of the pair of surrounding members adjacent to the guiding member;
an upper base member for fixing upper end surfaces of at least the pair of regulating members;
a first motor for horizontally moving the pair of moving members; and
a second motor for moving the N columnar members,
wherein the first motor is configured to horizontally move the pair of moving members over the same distance in opposite directions, thereby horizontally moving the pair of surrounding members over the same distance in opposite directions, the pair of surrounding members surrounding the N columnar members,
wherein the second motor is configured to move one columnar member of the N columnar members along an internal surface of a surrounding member of the pair of surrounding members surrounding the one columnar member, thereby moving the other N−1 columnar members sequentially along internal surfaces of the pair of surrounding members surrounding each of the other N−1 columnar members.

2. The X-ray collimator according to claim 1, wherein the pair of surrounding members is each configured to be horizontally movable along linear slides provided horizontally to the opposed surfaces of the pair of regulating members.

3. The X-ray collimator according to claim 1, wherein a bearing is interposed between upper ends of mutually facing surfaces of adjacent columnar members.

4. The X-ray collimator according to claim 1, wherein each of the N columnar members is provided with a stepped portion in a vertical direction.

5. The X-ray collimator according to claim 1, wherein each of the N columnar members is made of tungsten.

6. The X-ray collimator according to claim 1, wherein the substantially regular polygon shape is a substantially regular hexagonal shape, the N columnar members comprise six triangular prism members surrounded by the pair of surrounding members, each of the six triangular prism members having a planar shape obtained by dividing the substantially regular hexagonal shape into six equal parts, wherein the second motor is configured to move the six triangular prism members, wherein the first motor is driven to horizontally move the pair of moving members over the same distance in opposite directions, and thereby horizontally move the pair of surrounding members over the same distance in opposite directions, the pair of surrounding members surrounding the six triangular prism members, wherein the second motor is configured to move one triangular prism member of the six triangular prism members along an internal surface of a surrounding member of the pair of surrounding members surrounding the one triangular prism member, thereby sequentially moving the remaining five triangular prism members along internal surfaces of the pair of surrounding members surrounding each of the six triangular prism members.

7. The X-ray collimator according to claim 6, further comprising:

a first set of linear slides that couple together a first set of three triangular prism members having planar shapes combined to constitute one half of the substantially regular hexagonal shape and one of the pair of surrounding members, wherein each of the first set of three triangular prism members is configured to be horizontally movable with respect to each of three internal surfaces of the one surrounding member; and a second set of linear slides that couple together a second set of three triangular prism members constituting the other half of the substantially regular hexagonal shape and the other surrounding member, wherein each of the second set of three triangular prism members is configured to be horizontally movable with respect to each of three internal surfaces of the other surrounding member.

8. The X-ray collimator according to claim 1, further comprising:

a plate-like member with a horizontal surface provided on a vertical top side of the X-ray collimator;

a circular rotatable plate provided on a vertical bottom side of the plate-like member;

a motor block;

a third motor fixedly mounted on the motor block and configured to rotate the X-ray collimator, wherein the upper base member is configured to be fixed on the circular rotatable plate; and a belt bridges the third motor and the plate-like member.

* * * * *